US00H002283H

(19) United States
(12) Statutory Invention Registration
Stöhr et al.

(10) Reg. No.: US H2283 H
(43) Published: Sep. 3, 2013

(54) VACCINES FOR PROTECTING AGAINST INFLUENZA

(75) Inventors: Klaus Stöhr, Cambridge, MA (US); Philip Dormitzer, Weston, MA (US); Giuseppe Del Giudice, Siena (IT)

(73) Assignee: Novartis AG, Basel (CH)

(21) Appl. No.: 12/768,653

(22) Filed: Apr. 27, 2010

Related U.S. Application Data

(60) Provisional application No. 60/214,787, filed on Apr. 27, 2009, provisional application No. 60/216,198, filed on May 13, 2009, provisional application No. 60/238,628, filed on Aug. 31, 2009, and provisional application No. 60/279,665, filed on Oct. 22, 2009.

(51) Int. Cl.

| | |
|---|---|
| ***A61K 39/145*** | (2006.01) |
| ***A61K 39/295*** | (2006.01) |
| ***C12N 7/00*** | (2006.01) |
| ***A61P 31/16*** | (2006.01) |

(52) U.S. Cl. ..... 424/209.1; 424/206.1

(58) Field of Classification Search ..... 424/209.1, 424/206.1

See application file for complete search history.

(56) References Cited

U.S. PATENT DOCUMENTS

| | | | |
|---|---|---|---|
| 4,680,338 | A | 7/1987 | Sundoro |
| 4,689,338 | A | 8/1987 | Gerster |
| 4,929,624 | A | 5/1990 | Gerster et al. |
| 4,988,815 | A | 1/1991 | Andre et al. |
| 5,011,828 | A | 4/1991 | Goodman et al. |
| 5,238,944 | A | 8/1993 | Wick et al. |
| 5,266,575 | A | 11/1993 | Gerster et al. |
| 5,268,376 | A | 12/1993 | Gester |
| 5,346,905 | A | 9/1994 | Gerster |
| 5,352,784 | A | 10/1994 | Nikolaides et al. |
| 5,389,640 | A | 2/1995 | Gerster et al. |
| 5,395,937 | A | 3/1995 | Nikolaides et al. |
| 5,482,936 | A | 1/1996 | Lindstrom |
| 5,494,916 | A | 2/1996 | Lindstrom et al. |
| 5,525,612 | A | 6/1996 | Gerster |
| 5,658,731 | A | 8/1997 | Sproat et al. |
| 5,936,076 | A | 8/1999 | Higa et al. |
| 5,948,410 | A | 9/1999 | Van Scharrenburg et al. |
| 6,083,505 | A | 7/2000 | Miller et al. |
| 6,355,271 | B1 | 3/2002 | Bell et al. |
| 6,440,992 | B1 | 8/2002 | Gerster et al. |
| 6,468,544 | B1 | 10/2002 | Egorov et al. |
| 6,605,617 | B2 | 8/2003 | Renhowe et al. |
| 6,627,640 | B2 | 9/2003 | Gerster et al. |
| 6,649,372 | B1 | 11/2003 | Palese et al. |
| 6,656,938 | B2 | 12/2003 | Crooks et al. |
| 6,660,735 | B2 | 12/2003 | Crooks et al. |
| 6,660,747 | B2 | 12/2003 | Crooks et al. |
| 6,664,260 | B2 | 12/2003 | Charles et al. |
| 6,664,264 | B2 | 12/2003 | Dellaria et al. |
| 6,664,265 | B2 | 12/2003 | Crooks et al. |
| 6,667,312 | B2 | 12/2003 | Bonk et al. |
| 6,670,372 | B2 | 12/2003 | Charles et al. |
| 6,677,347 | B2 | 1/2004 | Crooks et al. |
| 6,677,348 | B2 | 1/2004 | Heppner et al. |
| 6,677,349 | B1 | 1/2004 | Griesgraber |
| 6,683,088 | B2 | 1/2004 | Crooks et al. |
| 6,703,402 | B2 | 3/2004 | Gerster et al. |
| 6,743,920 | B2 | 6/2004 | Lindstrom et al. |
| 6,800,624 | B2 | 10/2004 | Crooks et al. |
| 6,809,203 | B2 | 10/2004 | Gerster et al. |
| 6,888,000 | B2 | 5/2005 | Crooks et al. |
| 6,924,271 | B2 | 8/2005 | Averett et al. |
| 6,924,293 | B2 | 8/2005 | Lindstrom |
| 2005/0070556 | A1 | 3/2005 | Averett et al. |
| 2005/0192248 | A1 | 9/2005 | Tsuji et al. |
| 2005/0215517 | A1 | 9/2005 | Rossignol et al. |
| 2010/0010199 | A1 * | 1/2010 | Tsai et al. ..... 435/235.1 |

FOREIGN PATENT DOCUMENTS

| | | | |
|---|---|---|---|
| EP | 0870508 | B1 | 10/1998 |
| EP | 1260581 | A1 | 11/2002 |
| FR | 2859633 | A1 | 3/2005 |
| WO | WO-92/15582 | A1 | 9/1992 |
| WO | WO-95/18861 | A1 | 7/1995 |
| WO | WO-96/37624 | A1 | 11/1996 |
| WO | WO-97/37000 | A1 | 10/1997 |
| WO | WO-97/37001 | A1 | 10/1997 |
| WO | WO-98/46262 | A1 | 10/1998 |
| WO | WO-99/64068 | A1 | 12/1999 |
| WO | WO-00/60050 | A2 | 10/2000 |
| WO | WO-01/04333 | A1 | 1/2001 |

| | | | |
|---|---|---|---|
| WO | WO-01/21151 | A1 | 3/2001 |
| WO | WO-01/22972 | A2 | 4/2001 |
| WO | WO-01/22992 | A2 | 4/2001 |
| WO | WO-01/64846 | | 9/2001 |
| WO | WO-01/83794 | A2 | 11/2001 |
| WO | WO-01/85938 | A1 | 11/2001 |
| WO | WO-02/18383 | A2 | 3/2002 |
| WO | WO-02/28422 | A2 | 4/2002 |
| WO | WO-02/067983 | A1 | 9/2002 |
| WO | WO-02/074336 | A2 | 9/2002 |
| WO | WO-02/097072 | A1 | 12/2002 |
| WO | WO-03/011223 | A2 | 2/2003 |
| WO | WO-03/023021 | A2 | 3/2003 |
| WO | WO-03/023025 | A1 | 3/2003 |
| WO | WO-03/043415 | A1 | 5/2003 |
| WO | WO-03/076601 | A1 | 9/2003 |
| WO | WO-03/082272 | A1 | 10/2003 |
| WO | WO-03/105769 | A2 | 12/2003 |
| WO | WO-2004/018455 | A1 | 3/2004 |
| WO | WO-2004/060308 | A2 | 7/2004 |
| WO | WO-2004/064715 | A2 | 8/2004 |
| WO | WO-2004/064759 | A2 | 8/2004 |
| WO | WO-2004/087153 | A2 | 10/2004 |
| WO | WO-2005/042728 | A2 | 5/2005 |
| WO | WO-2005/102049 | A1 | 11/2005 |
| WO | WO-2005/113756 | A1 | 12/2005 |
| WO | WO-2005/113758 | A1 | 12/2005 |
| WO | WO-2006/027698 | A1 | 3/2006 |
| WO | WO-2006/067211 | A1 | 6/2006 |
| WO | WO-2006/071563 | A2 | 7/2006 |
| WO | WO-2006/108846 | A1 | 10/2006 |
| WO | WO-2007/002008 | A2 | 1/2007 |
| WO | WO-2007/052163 | A2 | 5/2007 |

OTHER PUBLICATIONS

Andrianov et al. (1998) *Biomaterials* 19:109–115.
Banzhoff (2000) *Immunology Letters* 71:91–96.
Beignon et al. (2002) *Infect Immun* 70:3012–3019.
Brands et al. (1999) *Dev Biol Stand* 98:93–100.
Briggs (1991) *J Parenter Sci Technol.* 45:7–12.
Bright et al. (2008) *PLoS ONE* 3:e1501.
Bruhl et al. (2000) *Vaccine* 19:1149–58.
Caillet et al. (2010) *Vaccine* 28:3076–3079.
Centers for Diseases Control and Prevention. (May 22, 2009) *MMWR* 58(19):521–56.
Chen et al. (2003) *Vaccine* 21:2830–2836.
Clark et al. (2009) *NEJM* 361:2424–35.
Cooper (1995) *Pharm Biotechnol* 6:559–80.
Couceiro & Baum (1994) *Mem Inst Oswaldo Cruz* 89(4):587–91.
Crevar & Ross (2008) *Virology Journal* 5(131), 9 pages.
de Jong et al. (2003) *Dev. Biol* (*Basel*) 115:63–73.
De Libero et al. (2005) *Nature Reviews Immunology* 5:485–496.
Del Giudice et al. (2009) *Sci Transl Med.* 1(12):1–3.
Dolin et al. (1977) *J Infect. Dis.* 136(Suppl.):S435–S442.
Doroshenko & Halperin (2009) *Expert Rev Vaccines* 8:679–88.
Dyakonova et al. (2004) *Int Immunopharmacol* 4(13):1615–23.
Efferson et at. (2006) *J Viral.* 80(1):383–94.
Ershler et al. (2007) *Ann N Y Acad Sci.* 1112:375–84.
Evans et al. (2003) *Expert Rev Vaccines* 2:219–229.
Galli et al. (2009) *PNAS USA* 106:7962–7.
Gambaryan & Matrosovich (1992) *J Virol Methods* 39(1–2):111–23.
Garten et al. (2009) *Science* 325:197–201.
GenBank sequence GI:325176, (Aug. 2, 1993), 1 page.
GenBank sequence GI:325237, (Aug. 2, 1993), 1 page.
Gennaro (2000) *Remington: The Science and Practice of Pharmacy.* 20th edition, ISBN: 0683306472.
Goff et al (2004) *J Am. Chem. Soc.* 126:13602–13603.
Greenbaum et at. (2004) *Vaccine* 22:2566–2577.
Greenberg et al. (2009) *NEJM* 361(25):2405–2413.
*Guidance for Industry: Bioanalytical Method Validation,* (May 2001). U.S. Department of Health and Human Services Food and Drug Administration Center for Drug Evaluation and Research (CDER) Center for Veterinary Medicine (CVM).
Halperin et al. (2002) *Vaccine* 20:1240–7.
Halperin et al. (1979) *Am J Public Health* 69:1247–1250.
Hehme et al. (2004) *Virus Res.* 103(1–2):163–171.
Herbert et al. (1979) *J Infect Dis* 140:234–238.
Herlocher et al. (2004) *J Infect Dis* 190(9):1627–30.
Hoffmann et al. (2002) *Vaccine* 20:3165–3170.
Hoffmann et al. (2000) *Virology* 267(2):310–7.
Huckriede et al. (2003) *Methods Enzymol* 373:74–91.
Hussain et al. (2010) *Vaccine* 28(22):3848–3855.
Ji et al. (2002) *Biotechniques* 32:1162–7.
Jin et al. (2003) *Virology* 306:18–24.
Johnson et al. (1999) *Bioorg Med Chem Lett* 9:2273–2278.
Jones (2003) *Curr Opin Invest Drugs* 4:214–218.
Keitel et al. (1996) *Clin Diagn Lab Immunol* 3:507–10.
Kistner et al. (1998) *Vaccine* 16:960–8.
Kistner et al. (1999) *Dev Biol Stand* 98:101–10.
Kistner et al. (2010) *PLoS ONE* 5(2): e9349.
Kitikoon et al. (2010) *Vaccine* 28:523–31.
Lahijani et al. (1998) *Hum Gene Ther.* 9:1173–80.
Liu et al. (2003) *Virology* 314:580–90.
Lokteff et al. (2001) *Biologicals* 29:123–32.
Lundblad (2001) *Biotechnology and Applied Biochemistry* 34:195–7.
Mann et al. (2004) *Vaccine* 2:2425–9.
Mastrosovich et al. (1999) *J Virol* 73:1146–55.
McCullers et al. (1999) *J Virol* 73:7343–8.
Meraldi et al. (2003) *Vaccine* 21:2485–2491.
Munster et al. (2009) *Science* 325:481–3.
Neumann et al. (2005) *Proc Natl Acad Sci USA* 102:16825–29.
Nony et al. (2001) *Vaccine* 27:3645–51.
Oki et al. (2004) *J Clin. Investig.* 113:1631–1640.
Ozaki et al. (2004) *J. Virol.* 78:1851–7.
Pajak et al. (2003) *Vaccine* 21:836–842.
Partidos et al. (1999) *Immunol Lett* 67:209–216.
Pau et al. (2001) *Vaccine* 19:2716–21.
Payne et al. (1998) *Adv Drug Delivery Review* 31:185–196.
Peppoloni et al. (2003) *Expert Rev Vaccines* 2:285–293.
Piascik (2003) *J Am Pharm Assoc* (*Wash DC*). 43:728–30.
Pine et al. (2002) *J Control Release* 85:263–270.
Pizza et al. (2000) *Int J Med Microbiol* 290:455–461.
Pizza et al. (2001) *Vaccine* 19:2534–2541.
Poole & Mussett (1989) *J Biol Stand* 17:161–71.
Poole et al. (1997) *J Endotoxin* Res 4:221–31.
Potter & Oxford (1979) *Br Med Bull* 35:69–75.
Quan et al. (2010) *PloS ONE* 5(2): e9161.
Roman et al. (2010) *Vaccine* 28:1740–45.
Ryan et al. (1999) *Infect Immun* 67:6270–6280.
Scharton–Kersten et al. (2000) *Infect Immun* 68:5306–5313.
Schellack et al. (2006) *Vaccine* 24:5461–72.
Signorelli & Hadden (2003) *Int Immunopharmacol* 3(8):1177–86.

Smith et al. (2009) *Nature* 459:1122–5.
Stanley (2002) *Clin Exp Dermatol* 27:571–577.
Stephenson et al. (2003) *Vaccine* 21:16887–93.
Stevens et al. (2006) *J Mol Biol* 355:1143–55.
Subbarao et al. (2003) *Virology* 305:192–200.
Talbot et al. (2008) *Vaccine* 26:4057–61.
Tebbey et al. (2000) *Vaccine* 18:2723–34.
Treanor et al. (1996) *J Infect Dis* 173:1467–70.
Tree et al. (2001) *Vaccine* 19:3444–50.
Powell & Newman, eds., (1995). *Vaccine Design: The Subunit and Adjuvant Approach* Plenum Press (ISBN 0–306–44867–X).
Plotkin & Orenstein, eds., (2004). *Vaccines*. 4th edition, ISBN: 0–7216–9688–0.
Vajo et al. (2010) *Lancet* 375:49–55.
Vasilakos et al. (2000) *Cell Immunol.* 204(1):64–74.
Webby et al. (2004) *Lancet* 363:1099–103.
Wong et al. (2003) *J Clin Pharmacol* 43(7):735–42.
Wu et al. (2004) *Antiviral Res.* 64(2):79–83.
Yang et al. (2004) *Anew. Chem. Int. Ed.* 43:3818–3822.
Zangwill et al. (2008) *J Infect Dis.* 197(4):580–3.
Zurbriggen et al. (2003) *Expert Rev Vaccines* 2:295–304.

* cited by examiner

*Primary Examiner*—Daniel Pihulic
(74) *Attorney, Agent, or Firm*—Morrison & Foerster LLP

(57) ABSTRACT

A vaccine containing a H1 subtype influenza A virus hemagglutinin is either unadjuvanted or is adjuvanted but not with an oil-in-water emulsion adjuvant. The vaccine is suitable for immunizing a patient against swine flu. The vaccine may be monovalent. The vaccine may include two different H1 subtype influenza A virus hemagglutinins, wherein (i) the first H1 subtype influenza A virus hemagglutinin is more closely related to SEQ ID NO: 1 than to SEQ ID NO: 3 and (ii) the second H1 subtype influenza A virus hemagglutinin is more closely related to SEQ ID NO: 3 than to SEQ ID NO: 1. A monovalent vaccine may be administered in conjunction with a trivalent A/H1N1-A/H3N2 B seasonal influenza vaccine. Other embodiments are also disclosed, such as reassortant viruses.

4 Claims, 7 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FIGURE 1
FIGURE 1A
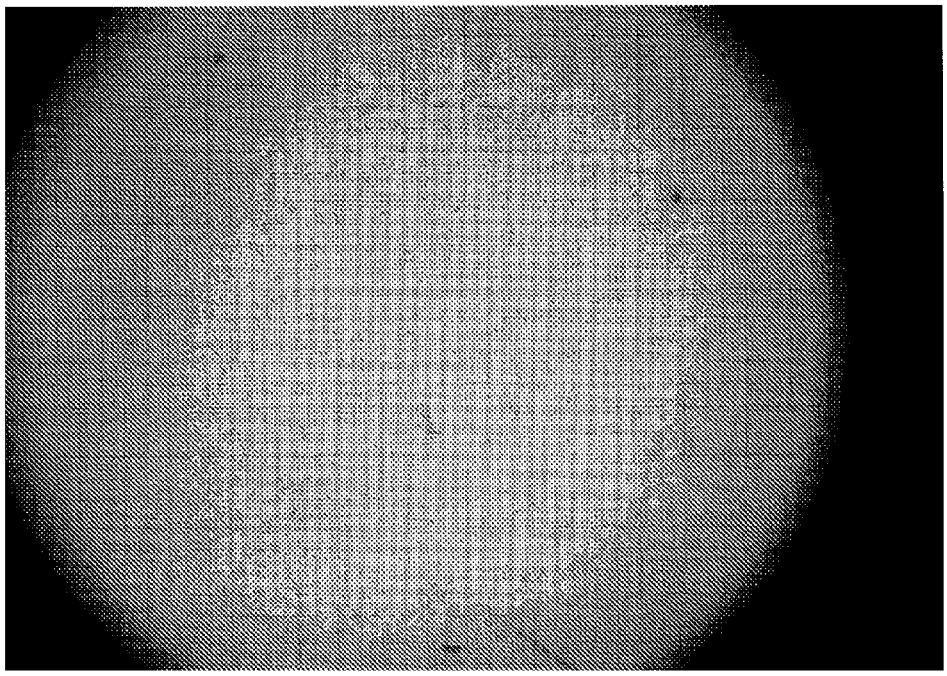
FIGURE 1B
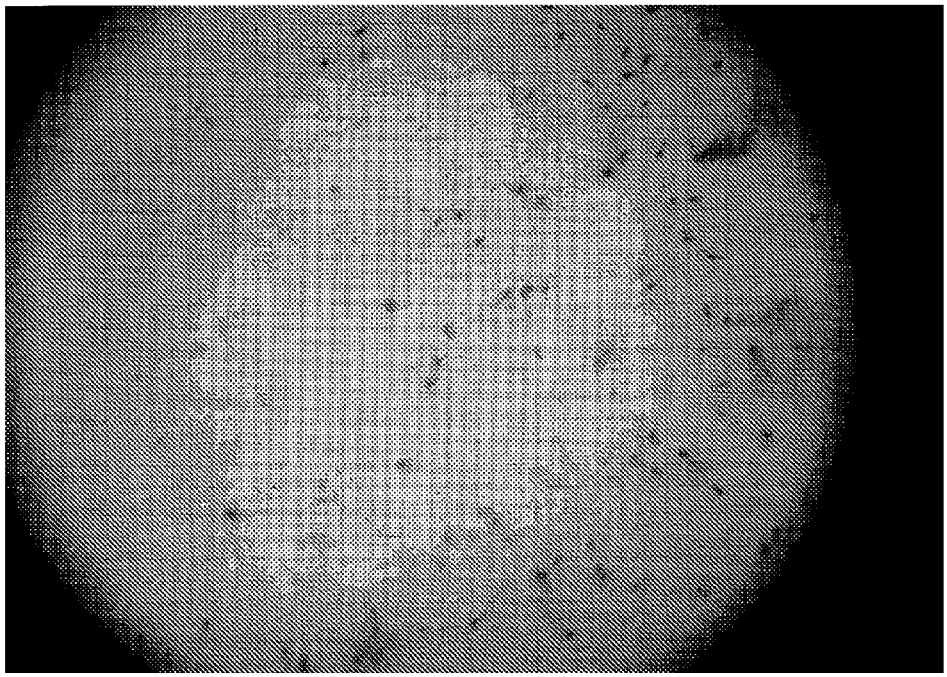

VACCINES FOR PROTECTING AGAINST INFLUENZA

This application claims the benefit of U.S. provisional applications 61/214,787 filed Apr. 27, 2009, 61/216,198 filed May 13, 2009, 61/238,628 filed Aug. 31, 2009, and 61/279,665 filed Oct. 22, 2009. No subject matter of these provisional applications has been inadvertently omitted from the present application.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002113000SEQLIST.txt, date recorded: Apr. 27, 2010, size: 52 KB).

TECHNICAL FIELD

This invention is in the field of vaccines for protecting against influenza virus infection, and in particular against strains such as the swine flu strain(s) which emerged in April 2009.

BACKGROUND ART

In April 2009 a human outbreak of swine flu was confirmed in many countries including Mexico and USA, and then spread rapidly across the globe. A pandemic was declared by the WHO in June 2009. The disease was caused by a newly identified swine influenza virus A/California/04/2009 A(H1N1). This swine flu strain seems to have no immunological cross-reactivity with current human influenza vaccines strains, including the A(H1N1) antigens in current human seasonal vaccines. The virus has been referred to variously as 'swine influenza', 'novel swine-origin H1N1 influenza', 'human-swine influenza', 'novel influenza A(H1N1)' and 'influenza A(H1N1)v'.

There is a need for a vaccine to prevent further human-to-human transmission of this swine flu and variants of it.

SUMMARY OF THE DISCLOSURE

The invention has various aspects. The invention disclosed and claimed herein does not encompass influenza vaccines having oil-in-water emulsion adjuvants, but it does encompass of unadjuvanted influenza vaccines and vaccines having alternative adjuvants i.e. adjuvants except for oil-in-water emulsions. Similarly, the invention disclosed herein does not encompass methods for manufacturing influenza vaccines, but it does encompass the vaccines themselves and their medical use. The invention also encompasses certain viruses.

According to a first aspect of the invention, a vaccine containing a H1 subtype influenza A virus hemagglutinin is adjuvanted, but not with an oil-in-water emulsion adjuvant. The hemagglutinin elicits an immune response in a recipient, and the adjuvant can enhance the heterovariant coverage of this response. Although a particular H1 antigen might not protect against swine flu on its own, the adjuvant can enhance the immune response so that protection is achieved even if the vaccine hemagglutinin shows only low immunological cross-reactivity with the swine flu hemagglutinin.

Furthermore, if the vaccine includes a hemagglutinin which is immunologically cross-reactive with the swine flu hemagglutinin then protection can be provided against the homologous strain and also against variants thereof, such as drift strains which can arise naturally.

Thus the invention provides a method for immunizing a patient (typically a human) against swine flu, comprising a step of administering to the patient a vaccine comprising (i) a H1 subtype influenza A virus hemagglutinin and (ii) an adjuvant, provided that the adjuvant is not an oil-in-water emulsion adjuvant. In some embodiments the H1 hemagglutinin is more closely related to SEQ ID NO: 1 than to SEQ ID NO: 3; in other embodiments it is more closely related to SEQ ID NO: 3 than to SEQ ID NO: 1.

The invention provides an immunogenic composition comprising (i) a H1 subtype influenza A virus hemagglutinin which is more closely related to SEQ ID NO: 1 than to SEQ ID NO: 3 and (ii) an adjuvant, provided that the adjuvant is not an oil-in-water emulsion adjuvant. This composition may be a monovalent vaccine (i.e. it includes hemagglutinin antigen from a single influenza virus strain) but in some embodiments it may be a multivalent vaccine e.g. a trivalent vaccine also including a H3N2 influenza A virus hemagglutinin and an influenza B virus hemagglutinin.

According to a second aspect of the invention, the invention provides an immunogenic composition comprising two different H1 subtype influenza A virus hemagglutinins, wherein (i) the first H1 subtype influenza A virus hemagglutinin is more closely related to SEQ ID NO: 1 than to SEQ ID NO: 3 and (ii) the second H1 subtype influenza A virus hemagglutinin is more closely related to SEQ ID NO: 3 than to SEQ ID NO: 1, and (iii) the composition is either adjuvanted or unadjuvanted, provided that when it is adjuvanted the adjuvant is not an oil-in-water emulsion adjuvant. This mixture of H1 hemagglutinins offers a broader spectrum of protection against H1 influenza A virus strains than currently available. This composition may also include (iii) a H3N2 and/or (iv) an influenza B virus antigen. In some embodiments, the composition includes (iii) a H3N2, (iv) a B/Victoria/2/87-like influenza B virus strain; and (v) a B/Yamagata/16/88-like influenza B virus strain. These compositions may include an immunological adjuvant, other than an oil-in-water emulsion adjuvant.

According to a third aspect of the invention, a monovalent vaccine containing a H1 subtype influenza A virus hemagglutinin is administered in conjunction with a trivalent A/H1N1-A/H3N2-B seasonal influenza vaccine, wherein the monovalent vaccine is either adjuvanted or unadjuvanted, provided that when it is adjuvanted the adjuvant is not an oil-in-water emulsion adjuvant. The monovalent vaccine includes a H1 subtype influenza A virus hemagglutinin which is more closely related to SEQ ID NO: 1 than to SEQ ID NO: 3; the trivalent vaccine includes a H1 subtype influenza A virus hemagglutinin which is more closely related to SEQ ID NO: 3 than to SEQ ID NO: 1. The monovalent vaccine may be administered before the trivalent vaccine, after the trivalent vaccine, or at the same time. Where the two vaccines are administered separately, there may be from 2-26 weeks between the administrations. The trivalent vaccine may be adjuvanted with an oil-in-water emulsion.

In one useful embodiment, a patient first receives the trivalent seasonal vaccine (preferably adjuvanted, such as the FLUAD™ product), and later receives the monovalent vaccine (adjuvanted, but not with an oil-in-water emulsion adjuvant, or unadjuvanted). As shown herein, pre-administration of a trivalent seasonal vaccine (particularly an adjuvanted one) can improve the efficacy of a monovalent H1N1 vaccine with a hemagglutinin more closely related to SEQ ID NO: 1 than to SEQ ID NO: 3.

In a related embodiment, a monovalent vaccine containing a H1 subtype influenza A virus hemagglutinin is administered in conjunction with a 4-valent A/H1N1-A/H3N2-B-B seasonal influenza vaccine, wherein the two B strains are a B/Victoria/2/87-like strain and a B/Yamagata/16/88-like strain, provided that the monovalent vaccine is not adjuvanted with an oil-in-water emulsion. The monovalent vaccine includes a H1 subtype influenza A virus hemagglutinin which is more closely related to SEQ ID NO: 1 than to SEQ ID NO: 3; the 4-valent vaccine includes a H1 subtype influenza A virus hemagglutinin which is more closely related to SEQ ID NO: 3 than to SEQ ID NO: 1. The monovalent vaccine may be administered before the trivalent vaccine, after the trivalent vaccine, or at the same time. Where the two vaccines are administered separately, there may be from 2-26 weeks between the administrations. The 4-valent vaccine (but not the monovalent vaccine) may e adjuvanted with an oil-in-water emulsion. In one useful embodiment, a patient first receives the monovalent vaccine and later receives the 4-valent vaccine.

According to a fourth aspect of the invention, a monovalent vaccine containing a H1 subtype influenza A virus hemagglutinin is administered by a two-dose regimen, provided that neither dose is adjuvanted with an oil-in-water emulsion (they may be unadjuvanted). The monovalent vaccine includes a H1 subtype influenza A virus hemagglutinin which is more closely related to SEQ ID NO: 1 than to SEQ ID NO: 3. The two doses are administered 1-6 weeks apart e.g. 1 week apart, 2 weeks apart, 3 weeks apart, 4 weeks apart, 5 weeks apart, 6 weeks apart. In some embodiments the H1 hemagglutinin is identical in both monovalent vaccines; in other embodiments the H1 hemagglutinins in the two monovalent vaccines have different amino acid sequences e.g. they may differ by up to 20 amino acids from each other (e.g. 1, 2, 3, 4, 5, 6, 7, 8, 9, 10, 11, 12, 13, 14, 15, 16, 17, 18, 19 or 20 amino acid substitutions).

According to a fifth aspect of the invention, an influenza A virus has a genome encoding a hemagglutinin with amino acid sequence SEQ ID NO: 6. Compared to SEQ ID NO: 1 this sequence has Pro-200 instead of Ser-200. This virus can be used with all embodiments discussed below. The invention also provides protein comprising amino acid sequence SEQ ID NO: 6. More generally, the invention provides an influenza A virus with a genome encoding a hemagglutinin which is more closely related to SEQ ID NO: 1 than to SEQ ID NO: 3, and which has a proline residue at the position corresponding to Ser-200 in SEQ ID NO: 1. This hemagglutinin may include a HA1 sequence with at least 90% (e.g ≧91%, ≧92%, ≧93%, ≧94%, ≧95%, ≧96%, ≧97%, ≧98%, ≧99%) identity to SEQ ID NO: 2, provided that it includes the Pro-200 residue.

According to a sixth aspect of the invention, an influenza A virus has a genome encoding a hemagglutinin with amino acid sequence SEQ ID NO: 7 or comprising SEQ ID NO: 8. Compared to SEQ ID NO: 1 this sequence has Glu-204 instead of Asp-204 and has a deletion of Lys-147. This virus can be used with all embodiments discussed below. The invention also provides protein comprising amino acid sequence SEQ ID NO: 7 or SEQ ID NO: 8.

The invention also provides an influenza A virus having a genome encoding a hemagglutinin with amino acid sequence SEQ ID NO: 9 or comprising SEQ ID NO: 10. Compared to SEQ ID NO: 7 this sequence has Ser-159 instead of Lys-159, Ser-206 instead of Gln-206, Ala-241 instead of Glu-241, and Glu-170 instead of Lys-170. This virus can be used with all embodiments discussed below. The invention also provides protein comprising amino acid sequence SEQ ID NO: 9 or SEQ ID NO: 10.

The invention also provides an influenza A virus having a genome encoding a hemagglutinin with amino acid sequence SEQ ID NO: 13. Compared to SEQ ID NO: 1 this sequence has Ile-208 instead of Leu-208. This virus can be used with all embodiments discussed below. The invention also provides protein comprising amino acid sequence SEQ ID NO: 13. More generally, the invention provides an influenza A virus with a genome encoding a hemagglutinin which is more closely related to SEQ ID NO: 1 than to SEQ ID NO: 3, and which has an isoleucine residue at the position corresponding to Leu-208 in SEQ ID NO: 1. This hemagglutinin may include a HA1 sequence with at least 90% (e.g ≧91%, ≧92%, ≧93%, ≧94%, ≧95%, ≧96%, ≧97%, ≧98%, ≧99%) identity to SEQ ID NO: 2, provided that it includes the Ile-208 residue.

The invention also provides an influenza A virus with a genome encoding a hemagglutinin which is more closely related to SEQ ID NO: 1 than to SEQ ID NO: 3, and which has one or more of (i) a proline residue at the position corresponding to Ser-200 in SEQ ID NO: 1, (ii) a glutamate residue at the position corresponding to Asp-204 in SEQ ID NO: 1, (iii) a serine residue at the position corresponding to Lys-159 in SEQ ID NO: 1, (iv) a serine residue at the position corresponding to Gln-206 in SEQ ID NO: 1, (v) an alanine residue at the position corresponding to Glu-241 in SEQ ID NO: 1, (vi) a glutamate residue at the position corresponding to Lys-170 in SEQ ID NO: 1, (vii) an isoleucine residue at the position corresponding to Leu-208 in SEQ ID NO: 1, and/or (viii) an aspartate residue at the position corresponding to Asn-173 in SEQ ID NO: 1. These viruses can be used with all embodiments discussed herein.

BRIEF DESCRIPTION OF THE DRAWINGS

FIG. 1 shows the results of a reverse genetics experiment.

FIG. 9 shows FFA titer (FFU/ml) against post-infection time (hours).

FIG. 10 shows HA titer against post-infection time.

FIG. 11 shows FFA titers for the five strains, and

FIG. 12 shows HA titers.

DETAILED DESCRIPTION OF EMBODIMENTS

Antigen components

Figure 2:
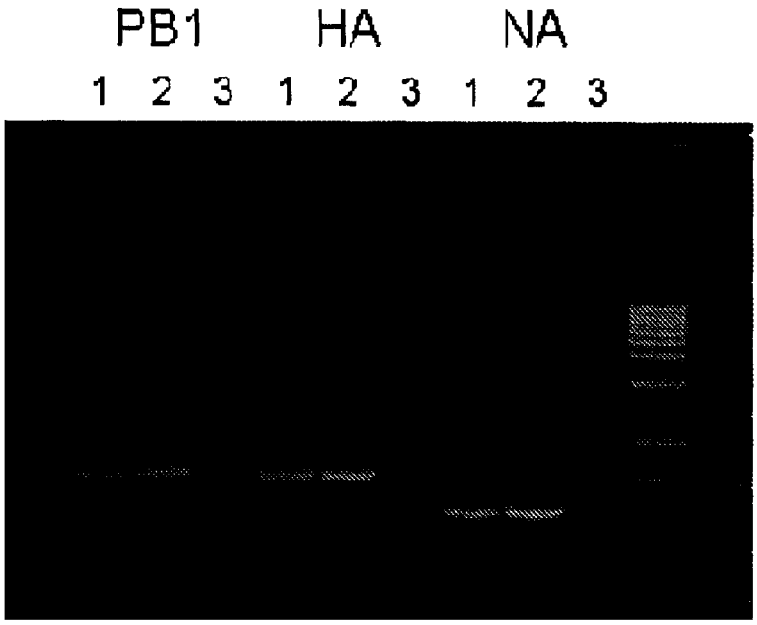
FIG. 2 shows the results of PCR amplification from rescued virus.

The invention uses influenza A virus hemagglutinin as a vaccine antigen. The antigen will typically be prepared from influenza virions but, as an alternative, haemagglutinin can be expressed in a recombinant host (e.g. in an insect cell line using a baculovirus vector) and used in purified form [1,2,3] or in the form of virus-like particles (VLPs; e.g. see references 4 and 5). In general, however, antigens will be from virions.

Various forms of influenza virus vaccine are currently available (e.g. see chapters 17 & 18 of reference 6). Vaccines are generally based either on live virus or on inactivated virus. Inactivated vaccines may be based on whole virions, 'split' virions, or on purified surface antigens. The antigen in vaccines of the invention may take the form of a live virus or, more preferably, an inactivated virus. Chemical means for inactivating a virus include treatment with an effective amount of one or more of the following agents: detergents, formaldehyde, formalin, β-propiolactone, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation.

Where an inactivated virus is used, the vaccine may comprise whole virion, split virion, or purified surface antigens (including hemagglutinin and, usually, also including neuraminidase). Split virion and purified surface antigens (i.e. subvirion vaccines) are particularly useful with the invention.

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses are well known in the art e.g. see refs. 7-12, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, AGRIPPAL™ and INFLUVAC™ products are subunit vaccines.

Influenza antigens can also be presented in the form of virosomes [13] (nucleic acid free viral-like liposomal particles), as in the INFLEXAL V™ and INVAVAC™ products, but it is preferred not to use virosomes with the present invention. Thus, in some embodiments, the influenza antigen is not in the form of a virosome.

The hemagglutinin antigen in the vaccine may be from any suitable strain. In some embodiments the hemagglutinin is one which, when administered to a human subject in unadjuvanted form, elicits anti-hemagglutinin antibodies which do not cross-react with A/California/04/2009 hemagglutinin (SEQ ID NO: 1; GI:227809830); in these embodiments the vaccine's adjuvant enhances the immune response such that a human subject produces antibodies which do cross-react with A/California/04/2009 hemagglutinin. In other embodiments the hemagglutinin is one which, when administered to a human subject in unadjuvanted form, can elicit anti-hemagglutinin antibodies which do cross-react with A/California/04/2009 hemagglutinin (SEQ ID NO: 1); in these embodiments the vaccine's adjuvant enhances the immune response such that a human subject produces a broader spectrum of antibodies, which can help to protect against drift strains of A/California/04/2009. In other embodiments the hemagglutinin is from A/California/04/2009 (SEQ ID NO: 1). In other embodiments the hemagglutinin comprises an HA1 amino acid sequence having at least i % sequence identity to SEQ ID NO: 2, where i is 85 or more e.g. 85, 88, 90, 92, 94, 95, 96, 97, 98, 99 or more (e.g. 100). Many such sequences are available e.g. from any of the following known strains:

A/swine/Guangxi/17/2005, A/Swine/Ohio/891/01, A/Swine/Indiana/9K035/99, A/Swine/Indiana/P12439/00, A/swine/Minnesota/1192/2001, A/SW/MN/23124-T/01, A/swine/Guangxi/13/2006, A/swine/Minnesota/00194/2, A/SW/MN/16419/01, A/Swine/Illinois/100085A/01, A/swine/OH/511445/2007, A/Swine/Illinois/100084/01, A/Swine/North Carolina/93523/01, A/Turkey/MO/24093/99, A/swine/Korea/PZ4/2006, A/swine/Korea/PZ7/2006, A/swine/Kansas/00246/2004, A/swine/Iowa/24297/1991, A/swine/Korea/CY08/2007, A/swine/Korea/JL02/2005, A/swine/Maryland/23239/1991, A/swine/Korea/S11/2005, A/turkey/IA/21089-3/1992, A/swine/Wisconsin/1915/1988, A/Swine/Iowa/930/01, A/swine/Korea/Hongsong2/2004, A/Ohio/3559/1988, A/swine/Iowa/17672/1988, A/turkey/NC/19762/1988, A/swine/St-Hyacinthe/106/1991, A/swine/Korea/JL04/2005, A/swine/Korea/JL01/2005, A/WI/4755/1994, A/swine/California/T9001707/1991, A/swine/Korea/Asan04/2006, A/MD/12/1991, A/Swine/Wisconsin/235/97, A/swine/Kansas/3228/1987, A/Swine/Indiana/1726/1988, A/swine/Ontario/11112/04, A/Swine/Wisconsin/163/97, A/SW/MO/1877/01, A/swine/Shanghai/3/2005, A/turkey/NC/17026/1988, A/swine/Iowa/31483/1988, A/swine/Guangdong/2/01, A/swine/Iowa/1/1987, A/swine/Iowa/3/1985, A/swine/Tennessee/31/1977, etc.

Further H1N1 strains with suitable HA antigens include A/California/04/2009 itself, A/California/7/2009, A/Texas/5/2009, A/England/195/2009, and A/New York/18/2009.

Preferred embodiments comprise a hemagglutinin which, when administered to a human subject in unadjuvanted form, can elicit anti-hemagglutinin antibodies which cross-react with A/California/04/2009 hemagglutinin (SEQ ID NO: 1), such as hemagglutinins comprising an amino acid sequence having at least i % sequence identity to SEQ ID NO: 2 as discussed above.

In some embodiments, the hemagglutinin is more closely related to SEQ ID NO: 1 (A/California/04/2009) than to SEQ ID NO: 3 (A/Chile/1/1983); in other embodiments, the hemagglutinin is more closely related to SEQ ID NO: 3 than to SEQ ID NO: 1. A hemagglutinin which is more closely related to SEQ ID NO: 1 than to SEQ ID NO: 3 (i.e. has a higher degree sequence identity when compared to SEQ ID NO: 1 than to SEQ ID NO: 3 using the same algorithm and parameters) is referred to hereafter as a 'H1*' hemagglutinin. SEQ ID NOs: 1 and 3 are 80.4% identical.

Useful full-length H1 hemagglutinin sequences for use with the invention include SEQ ID NO: 1, SEQ ID NO: 6, SEQ ID NO: 7, SEQ ID NO: 9, SEQ ID NO: 11, as well as those comprising an amino acid sequence having at least i % sequence identity to SEQ ID NO: 2 as discussed above, or having at least i % sequence identity to SEQ ID NO: 12. Ideally the hemagglutinin does not include a hyper-basic regions around the HA1/HA2 cleavage site. Preferred hemagglutinins have a binding preference for oligosaccharides with a Sia(α2,6)Gal terminal disaccharide compared to oligosaccharides with a Sia(α2,3)Gal terminal disaccharide (see below).

SEQ ID NO: 11 (comprising SEQ ID NO: 12) is a useful H1* hemagglutinin. It differs from SEQ ID NO: 1 at residues 214, 226 and 240 (i.e. 99.47% identity).

As well as including a H1 hemagglutinin (such as a H1* hemagglutinin), compositions of the invention may include antigen(s) from one or more (e.g. 1, 2, 3, 4 or more) additional influenza virus strains, including influenza A virus and/or influenza B virus. Thus a composition may include antigen from one or more strains characteristics of a normal seasonal vaccine plus at least one H1* hemagglutinin e.g. a 4-valent vaccine with two H1 strains (one a H1* hemagglutinin, one not a H1* hemagglutinin), a H3N2 strain, and one influenza B strain, or a 5-valent vaccine with two H1 strains (one a H1* hemagglutinin, one not a H1* hemagglutinin), a H3N2 strain, and two influenza B virus strains (a B/Victoria/2/87-like strain and a B/Yamagata/16/88-like strain). The invention also provides a 2-valent vaccine comprising a H1* hemagglutinin and a H5 hemagglutinin. Where a vaccine includes more than one strain of influenza, the different strains are typically grown separately and are mixed after the viruses have been harvested and antigens have been prepared. Thus a process of the invention may include the step of mixing antigens from more than one influenza strain.

Where a vaccine of the invention includes two influenza B strains, one B/Victoria/2/87-like strain and one B/Yamagata/16/88-like strain will be included. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [14]. In some embodiments of the invention where antigens are present from two or more influenza B virus strains, at least two of the influenza B virus strains may have distinct hemagglutinins but related neuraminidases. For instance, they may both have a B/Victoria/2/87-like neuraminidase [15] or may both have a B/Yamagata/16/88-like neuraminidase. For instance, two B/Victoria/2/87-like neuraminidases may both have one or more of the following sequence characteristics: (1) not a serine at residue 27, but preferably a leucine; (2) not a glutamate at residue 44, but preferably a lysine; (3) not a threonine at residue 46, but preferably an isoleucine; (4) not a proline at residue 51, but at preferably a serine; (5) not an arginine at residue 65, but preferably a histidine; (6) not a glycine residue 70, but preferably a glutamate; (7) not a leucine at residue 73, but preferably a phenylalanine; and/or (8) not a proline at residue 88, but preferably a glutamine. Similarly, in some embodiments the neuraminidase may have a deletion at residue 43, or it may have a threonine; a deletion at residue 43, arising from a trinucleotide deletion in the NA gene, has been reported as a characteristic of B/Victoria/2/87-like strains, although recent strains have regained Thr-43 [15]. Conversely, of course, the opposite characteristics may be shared by two B/Yamagata/16/88-like neuraminidases e.g. S27, E44, T46, P51, R65, G70, L73, and/or P88. These amino acids are numbered relative to the 'Lee40' neuraminidase sequence [16].

An influenza virus from which hemagglutinin protein is purified may be attenuated.

The influenza virus may be temperature-sensitive. The influenza virus may be cold-adapted. These three features are particularly useful when using live virus as an antigen.

The influenza virus may be resistant to antiviral therapy (e.g. resistant to oseltamivir [17] and/or zanamivir).

In some embodiments, strains used with the invention will thus have hemagglutinin with a binding preference for oligosaccharides with a Sia(α2,6)Gal terminal disaccharide compared to oligosaccharides with a Sia(α2,3)Gal terminal disaccharide. Human influenza viruses bind to receptor oligosaccharides having a Sia(α2,6)Gal terminal disaccharide (sialic acid linked α-2,6 to galactose), but eggs and Vero cells have receptor oligosaccharides with a Sia(α2,3)Gal terminal disaccharide. Growth of human influenza viruses in cells such as MDCK provides selection pressure on hemagglutinin to maintain the native Sia(α2,6)Gal binding, unlike egg passaging. To determine if a virus has a binding preference for oligosaccharides with a Sia(α2,6)Gal terminal disaccharide compared to oligosaccharides with a Sia(α2,3)Gal terminal disaccharide, various assays can be used. For instance, reference 18 describes a solid-phase enzyme-linked assay for influenza virus receptor-binding activity which gives sensitive and quantitative measurements of affinity constants. Reference 19 used a solid-phase assay in which binding of viruses to two different sialylglycoproteins was assessed (ovomucoid, with Sia(α2,3)Gal determinants; and pig $\alpha_2$-macroglobulin, which Sia(α2,6)Gal determinants), and also describes an assay in which the binding of virus was assessed against two receptor analogs: free sialic acid (Neu5Ac) and 3'-sialyllactose (Neu5Acα2-3Galβ1-4Glc). Reference 20 reports an assay using a glycan array which was able to clearly differentiate receptor preferences for α2,3 or α2,6 linkages. Reference 21 reports an assay based on agglutination of human erythrocytes enzymatically modified to contain either Sia(α2,6)Gal or Sia(α2,3)Gal. Depending on the type of assay, it may be performed directly with the virus itself, or can be performed indirectly with hemagglutinin purified from the virus.

In some embodiments the H1 hemagglutinin has a different glycosylation pattern from the patterns seen in egg-derived viruses. Thus the HA (and other glycoproteins) may include glycoforms that are not seen in chicken eggs. Useful HA includes canine glycoforms.

In addition to including hemagglutinin antigen, vaccines of the invention typically also include a neuraminidase protein e.g. the vaccine will include viral neuraminidase. The invention may protect against one or more of influenza A virus NA subtypes N1, N2, N3, N4, N5, N6, N7, N8 or N9, but it will usually be against N (e.g. a H1N1 virus) or N2 (e.g. a H1N2 virus). Whole virions, split virions and subunit vaccines all include both hemagglutinin and neuraminidase. When a vaccine includes a neuraminidase antigen, the neuraminidase may have at least j % sequence identity to SEQ ID NO: 4, where j is 75 or more e.g. 75, 80, 85, 88, 90, 92, 94, 95, 96, 97, 98, 99 or more (e.g. 100). Many such sequences are available. In some embodiments, the neuraminidase is more closely related to SEQ ID NO: 4 than to SEQ ID NO: 5. SEQ ID NOs: 4 and 5 are 82% identical.

Vaccines may also include a matrix protein, such as M1 and/or M2 (or a fragment thereof), and/or nucleoprotein. A pig model has shown that addition of M2 to inactivated H1N1swine influenza virus vaccine (adjuvanted with an oil-in-water emulsion) can enhance the vaccines efficacy [22].

The influenza virus may be a reassortant strain, and may have been obtained by reverse genetics techniques. Reverse genetics techniques [e.g. 23-27] allow influenza viruses with desired genome segments to be prepared in vitro using plasmids, or by plasmid-free systems. Typically, the technique involves expressing (a) DNA molecules that encode desired viral RNA molecules e.g. from polI promoters, and (b) DNA molecules that encode viral proteins e.g. from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA are preferred [28-30], and these methods will also involve the use of plasmids to express all or some (e.g. just the PB1, PB2, PA and NP proteins) of the viral proteins, with up to 12 plasmids being used in some methods. If canine cells are used, a canine polI promoter may be used [31].

To reduce the number of plasmids needed, one approach [32] combines a plurality of RNA polymerase I transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). The method may involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using polI promoters to encode the viral RNA segments, it is possible to use bacteriophage polymerase promoters [33]. For instance, promoters for the SP6, T3 or T7 polymerases can conveniently be used. Because of the species-specificity of polI promoters, bacteriophage polymerase promoters can be more convenient for many cell types (e.g. MDCK), although a cell must also be transfected with a plasmid encoding the exogenous polymerase enzyme.

In other techniques it is possible to use dual polI and polII promoters to simultaneously code for the viral RNAs and for expressible mRNAs from a single template [34,35].

An influenza A virus may include one or more RNA segments from a A/PR/8/34 virus (typically 6 segments from A/PR/8/34, with the HA and N segments being from a vaccine strain, i.e. a 6:2 reassortant), particularly when viruses are grown in eggs. It may also include one or more RNA segments from a A/WSN/33 virus, or from any other virus strain useful for generating reassortant viruses for vaccine preparation. The inclusion of A/Ann Arbor backbone segments is also useful, particularly for live vaccines. Typically, the invention protects against a strain that is capable of human-to-human transmission, and so the strain's genome will usually include at least one RNA segment that originated in a mammalian (e.g. in a human) influenza virus.

The viruses used as the source of the antigens can be grown either on eggs or on cell culture. The current standard method for influenza virus growth uses specific pathogen-free (SPF) embryonated hen eggs, with virus being purified from the egg contents (allantoic fluid). More recently, however, viruses have been grown in animal cell culture and, for reasons of speed and patient allergies, this growth method is preferred. If egg-based viral growth is used then one or more amino acids may be introduced into the allantoid fluid of the egg together with the virus [12].

When cell culture is used, the viral growth substrate will typically be a cell line of mammalian origin. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc.. Preferred mammalian cell lines for growing influenza viruses include: MDCK cells [36-39], derived from Madin Darby canine kidney; Vero cells [40-42], derived from African green monkey (*Cercopithecus aethiops*) kidney; or PER.C6 cells [43], derived from human embryonic retinoblasts. These cell lines are widely available e.g. from the American Type Cell Culture (ATCC) collection, from the Coriell Cell Repositories, or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 44-46], including cell lines derived from ducks (e.g. duck retina) or hens. Examples of avian cell lines include avian embryonic stem cells [44,47] and duck retina cells [45]. Suitable avian embryonic stem cells, include the EBx cell line derived from chicken embryonic stem cells, EB45, EB14, and EB14-074 [48]. Chicken embryo fibroblasts (CEF) may also be used.

The most preferred cell lines for growing influenza viruses are MDCK cell lines. The original MDCK cell line is available from the ATCC as CCL-34, but derivatives of this cell line may also be used. For instance, reference 36 discloses a MDCK cell line that was adapted for growth in suspension culture ('MDCK 33016', deposited as DSM ACC 2219). Similarly, reference 49 discloses a MDCK-derived cell line that grows in suspension in serum-free culture ('B-702', deposited as FERM BP-7449). Reference 50 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 51 discloses MDCK cell lines with high susceptibility to infection, including 'MDCK.5F1' cells (ATCC CRL-12042). Any of these MDCK cell lines can be used.

Where virus has been grown on a mammalian cell line then the composition will advantageously be free from egg proteins (e.g. ovalbumin and ovomucoid) and from chicken DNA, thereby reducing allergenicity.

Where virus has been grown on a cell line then the culture for growth, and also the viral inoculum used to start the culture, will preferably be free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [52]. Absence of herpes simplex viruses is particularly preferred.

For growth on a cell line, such as on MDCK cells, virus may be grown on cells in suspension [36, 53, 54] or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. [55] during viral replication e.g. 30-36° C., at 31-35° C., or at 33±1° C.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

Haemagglutinin (HA) is the main immunogen in inactivated influenza vaccines, and vaccine doses are standardised by reference to HA levels, typically as measured by a single radial immunodiffusion (SRID) assay. Current vaccines typically contain about 15 μg of HA per strain, although lower doses are also used e.g. for children, or in emergency situations. Fractional doses such as ½ (i.e. 7.5 μg HA per strain, as in FOCETRIA™), ¼ (i.e. 3.75 μg per strain, as in PREPANDRIX™) and ⅛ have been used [56,57], as have higher doses (e.g. 3x or 9x doses [58,59]).Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, 3.75-15 μg etc. Particular doses include e.g. about 45, about 30, about 15, about 10, about 7.5, about 5, about 3.8, about 3.75, about 1.9, about 1.5, etc. μg per strain. An equal HA mass per strain is typical. Lower doses (i.e. <15 μg/dose) are most useful when an adjuvant is present in the vaccine, as with the invention. Although doses as high as 90 μg have been used in some studies (e.g. reference 60), compositions of the invention will usually include 15 μg/dose/strain or less.

HA used with the invention may be a natural HA as found in a virus, or may have been modified.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

Compositions of the invention may include detergent e.g. a polyoxyethylene sorbitan ester surfactant (known as 'Tweens' e.g. polysorbate 80), an octoxynol (such as octoxynol-9 (Triton X-100) or 10, or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol-10, α-tocopheryl hydrogen succinate and polysorbate 80. Other residual components in trace amounts could be antibiotics (e.g. neomycin, kanamycin, polymyxin B).

Host cell DNA

Where virus has been grown on a cell line then it is standard practice to minimize the amount of residual cell line DNA in the final vaccine, in order to minimize any oncogenic activity of the DNA. Thus the composition preferably contains less than 10 ng (preferably less than 1 ng, and more preferably less than 100 pg) of residual host cell DNA per dose, although trace amounts of host cell DNA may be present. In general, the host cell DNA that it is desirable to exclude from compositions of the invention is DNA that is longer than 100 bp.

Measurement of residual host cell DNA is now a routine regulatory requirement for biologicals and is within the normal capabilities of the skilled person. The assay used to measure DNA will typically be a validated assay [61,62]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three principle techniques for DNA quantification can be used: hybridization methods, such as Southern blots or slot blots [63]; immunoassay methods, such as the Threshold™ System [64]; and quantitative PCR [65]. These methods are all familiar to the skilled person, although the precise characteristics of each method may depend on the host cell in question e.g. the choice of probes for hybridization, the choice of primers and/or probes for amplification, etc. The Threshold™ system from *Molecular Devices* is a quantitative assay for picogram levels of total DNA, and has been used for monitoring levels of contaminating DNA in biopharmaceuticals [64]. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 66.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 67 & 68, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [69] while avoiding use of formaldehyde.

Vaccines containing <10 ng (e.g. <1 ng, <100 pg) host cell DNA per 15 μg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 μg of haemagglutinin are more preferred, as are vaccines containing <10 ng (e.g. <1 ng, <100 pg) host cell DNA per 0.5 ml volume.

Adjuvants

Compositions of the invention can include an adjuvant which can function to enhance the immune responses (humoral and/or cellular) elicited in a patient who receives the composition, but they do not include an oil-in-water emulsion (e.g. as in the FLUAD™ product from Chiron Vaccines). Instead of using oil-in-water emulsion adjuvants, other adjuvants can also be used with the invention. Thus, for instance, any of the following adjuvants may be used:

The adjuvants known as aluminum hydroxide and aluminum phosphate. These names are conventional, but are used for convenience only, as neither is a precise description of the actual chemical compound which is present (e.g. see chapter 9 of reference 70). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. The invention can use a mixture of both an aluminium hydroxide and an aluminium phosphate. In this case there may be more aluminium phosphate than hydroxide e.g. a weight ratio of at least 2:1 e.g. ≧5:1, ≧6:1, ≧7:1, ≧8:1, ≧9:1, etc.

Calcium salts, such as calcium phosphates (e.g. the "CAP" particles disclosed in ref. 71). Nanoparticulate calcium phosphate salts are useful e.g. with a diameter between about 300 nm and about 4000 nm.

Saponin formulations such as QS21 or ISCOMs (including QS21-containing ISCOMs). ISCOMs may comprise cholesterols.

Non-toxic derivatives of enterobacterial lipopolysaccharide (LPS), or lipid A derivatives. Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. Other non-toxic LPS derivatives include monophosphoryl lipid A mimics, such as aminoalkyl glucosaminide phosphate derivatives e.g. RC-529 [72,73]. Lipid A derivatives include derivatives of lipid A from *Escherichia coli* such as OM-174. OM-174 is described for example in refs. 74 & 75.

Immunostimulatory oligonucleotides. These may contain a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory. A useful CpG adjuvant is CpG7909, also known as ProMune™ (Coley Pharmaceutical Group, Inc.). Another is CpG1826. As an alternative, or in addition, to using CpG sequences, TpG sequences can be used [76], and these oligonucleotides may be free from unmethylated CpG motifs. A particularly useful adjuvant based around immunostimulatory oligonucleotides is known as IC-31™ [77]. Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence (s).

An ADP-ribosylating toxin or detoxified derivative thereof e.g. LT-K63 or LT-R72 [78-85CT-E29H [86].

Chitosan.

Microparticles (i.e. a particle of ~100 nm to ~150 μm in diameter, more preferably ~~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

Liposomes.

A phosphazene, such as poly[di(carboxylatophenoxy) phosphazene] ("PCPP") [87,88].

Imidazoquinolones e.g. Imiquimod ("R-837") [89,90], Resiquimod ("R-848") [91], and their analogs; and salts thereof (e.g. the hydrochloride salts). Further details about immunostimulatory imidazoquinolines can be found in references 92 to 96.

Substituted ureas [97], such as 'ER 803058', 'ER 803732', 'ER 804053', ER 804058', 'ER 804059', 'ER 804442', 'ER 804680', 'ER 804764', ER 803022 or 'ER 804057'.

Cyclic diguanylate ('c-di-GMP').

A thiosemicarbazone compound, such as those disclosed in reference 98.

A tryptanthrin compound, such as those disclosed in reference 99.

A nucleoside analog, such as: (a) Isatorabine (ANA-245; 7-thia-8-oxoguanosine) and prodrugs thereof; (b) ANA975; (c) ANA-025-1; (d) ANA380; (e) the compounds disclosed in references 100 to 102Loxoribine (7-allyl-8-oxoguanosine) [103].

Compounds disclosed in reference 104, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [105,106], Hydrapthalamide compounds, Benzophenone compounds, Isoxazole compounds, Sterol compounds, Quinazilinone compounds, Pyrrole compounds [107], Anthraquinone compounds, Quinoxaline compounds, Triazine compounds, Pyrazalopyrimidine compounds, and Benzazole compounds [108].

Compounds containing lipids linked to a phosphate-containing acyclic backbone, such as the TLR4 antagonist E5564 [109,110]:

A polyoxidonium polymer [111,112] or other N-oxidized polyethylene-piperazine derivative.

Methyl inosine 5'-monophosphate ("MIMP") [113].

A polyhydroxlated pyrrolizidine compound [114].

A CD1d ligand, such as an α-glycosylceramide [115-122] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

An inulin, such as a gamma inulin [123] or derivative thereof, such as algammulin.

Pharmaceutical compositions

Compositions of the invention are pharmaceutically acceptable. They usually include components in addition to the antigens e.g. they typically include one or more pharmaceutical carrier(s) and/or excipient(s). A thorough discussion of such components is available in reference 124.

Compositions will generally be in aqueous form.

The composition may include preservatives such as thiomersal (e.g at 10 μg/ml) or 2-phenoxyethanol. It is preferred, however, that the vaccine should be substantially free from (i.e. less than 5 μg/ml) mercurial material e.g. thiomersal-free [125]. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [126], but keeping osmolality in this range is nevertheless preferred.

Compositions may include one or more buffers. Typical buffers include: a phosphate buffer; a Tris buffer; a borate buffer; a succinate buffer; a histidine buffer; or a citrate buffer. Buffers will typically be included in the 5-20 mM range. The buffer may be in an emulsion's aqueous phase.

The pH of a composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The composition is preferably sterile. The composition is preferably gluten free.

Preferred vaccines have a low endotoxin content e.g. less than 1 IU/ml, and preferably less than 0.5 IU/ml. The international unit for endotoxin measurement is well known and can be calculated for a sample by, for instance, comparison to an international standard [127,128], such as the 2nd International Standard (Code 94/580-IS) available from the NIBSC. Current vaccines prepared from virus grown in eggs have endotoxin levels in the region of 0.5-5 IU/ml.

The vaccine is preferably free from antibiotics (e.g. neomycin, kanamycin, polymyxin B).

The composition may include material for a single immunisation, or may include material for multiple immunisations (i.e. a 'multidose' composition). Multidose arrangements usually include a preservative in the vaccine. To avoid this need, a vaccine may be contained in a container having an aseptic adaptor for removal of material.

Influenza vaccines are typically administered in a dosage volume of about 0.5 ml, although a half dose (i.e. about 0.25 ml) may be administered to children, and unit doses will be selected accordingly e.g. a unit dose to give a 0.5 ml dose for administration to a patient.

Packaging of compositions or kit components

Processes of the invention can include a step in which vaccine is placed into a container, and in particular into a container for distribution for use by physicians.

Suitable containers for the vaccines include vials, nasal sprays and disposable syringes, which should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial, and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a composition/component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A composition may be combined (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of treatment, and administration of the vaccine

Compositions of the invention are suitable for administration to human patients, and the invention provides a method of raising an immune response in a patient, comprising the step of administering a composition of the invention to the patient.

The invention also provides a kit or composition of the invention for use as a medicament.

The immune response raised by the methods and uses of the invention will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 3040 gives around 50% protection from infection by a homologous virus) [129]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [130-132], intradermal [133,134], oral [135], transcutaneous, transdermal [136], etc. Intradermal and intranasal routes are attractive. Intradermal administration may involve a microinjection device e.g. with a needle about 1.5 mm long.

Vaccines prepared according to the invention may be used to treat both children and adults. Influenza vaccines are currently recommended for use in pediatric and adult immunisation, from the age of 6 months. Thus the patient may be less than 1 year old (e.g. <6 months old), 1-5 years old, 5-15 years old, 15-55 years old, or at least 55 years old. Preferred patients for receiving the vaccines are the elderly (e.g. ≧50 years old, ≧60 years old, and preferably ≧65 years), the young (e.g. ≦5 years old, or those aged between 6 months and 24 years, or between 6 months and 4 years, or between 5-18 years), middle aged (25-64 years old), hospitalised patients, healthcare workers, armed service and military personnel, pregnant women, the chronically ill, immunodeficient patients, patients who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population.

Some older adults (about a third of those older than 60 years) but few young adults and essentially no children have pre-existing serum antibody against the pandemic A/CA/04/09 strain. Seasonal immunization of young people does not elicit antibodies against this strain [137]. A useful group of subjects to receive immunogenic compositions of the invention, particularly such compositions comprising an oil-in-water adjuvant, is those subjects who have no existing serum antibody against the pandemic A/CA/04/09 strain e.g. patients born after 1960, after 1970, after 1980, after 1990, or after 2000.

Preferred compositions of the invention satisfy 1, 2 or 3 of the CPMP criteria for efficacy. In adults (18-60 years), these criteria are: (1) ≧70% seroprotection; (2) ≧40% seroconversion; and/or (3) a GMT increase of ≧2.5-fold. In elderly (>60 years), these criteria are: (1) ≧60% seroprotection; (2) ≧30% seroconversion; and/or (3) a GMT increase of ≧2-fold. These criteria are based on open label studies with at least 50 patients. The criteria apply for each strain in a vaccine.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype. Multiple doses will typically be administered at least 1 week apart (e.g. about 2 weeks, about 3 weeks, about 4 weeks, about 6 weeks, about 8 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H.influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™). Another antiviral which can be administered is thymosin alpha 1 (e.g. thymalfasin, a 28 amino acid synthetic peptide, available as ZADAXIN™), particularly when used in combination with a vaccine which includes an oil-in-water emulsion adjuvant [138]. In one specific embodiment, a patient receives a neuraminidase inhibitor, such as oseltamivir phosphate, at substantially the same time as receiving an inactivated whole virion vaccine (e.g. monovalent, H1*).

Vaccine products and kits

The invention also provides an unadjuvanted vaccine comprising a H1 subtype influenza A virus hemagglutinin which is more closely related to SEQ ID NO: 1 than to SEQ ID NO: 3. This composition is a monovalent inactivated surface antigen vaccine. The inactivated viruses may have been grown on eggs or in MDCK cell culture. The vaccine has a unit dose including about 15 μg of the H1 hemagglutinin (e.g. a A/California/7/2009-like strain, such as from reassortant strain X179A). The vaccine is unadjuvanted. It may be administered intramuscularly e.g. to the deltoid or anterolateral thigh. A subject may receive a single dose of the vaccine or may receive two doses (e.g. separated by between 2 weeks and 6 months e.g. 3 weeks apart).

The invention also provides a vaccine comprising (i) a H1 subtype influenza A virus hemagglutinin which is more closely related to SEQ ID NO: 1 than to SEQ ID NO: 3 and (ii) an adjuvant comprising both aluminium phosphate and aluminium hydroxide. In a useful embodiment, this composition is a monovalent inactivated whole virion vaccine. The inactivated viruses may have been grown on eggs. The vaccine may be presented in a syringe containing a 0.5 ml unit dose, with each unit dose including about 15 μg of the H1 hemagglutinin. The adjuvant may include, in a 0.5 ml volume, about 0.5 mg of $Al^{+++}$ e.g. 0.45 mg from aluminium phosphate and 0.05 mg from aluminium hydroxide, hydrated. The composition may include 50 μg of thiomersal.

The invention also provides a vaccine comprising (i) a H1 subtype influenza A virus hemagglutinin which is more closely related to SEQ ID NO: 1 than to SEQ ID NO: 3 and (ii) an aluminium phosphate adjuvant. In a useful embodiment, this composition is a monovalent inactivated whole virion vaccine (e.g. obtained by formaldehyde inactivation). The inactivated viruses may have been grown on eggs. The vaccine may be presented in an ampoule containing a 0.5 ml unit dose, with each unit dose including about 6 μg of the H1 hemagglutinin (e.g. from a reassortant strain, such as X-179A). The hemagglutinin may be adsorbed to the aluminium phosphate adjuvant, which may be in the form of a gel. The composition may include thiomersal.

The invention also provides an unadjuvanted vaccine comprising a H1 subtype influenza A virus hemagglutinin which is more closely related to SEQ ID NO: 1 than to SEQ ID NO: 3 (e.g. from a A/California/7/2009 strain). In a useful embodiment, this composition is a monovalent inactivated whole virion vaccine in which the inactivated viruses were grown on Vero cells. The vaccine may be presented in a vial containing multiple doses e.g. 10×0.5 ml unit dose, with each unit dose including about 7.5 μg of the H1 hemagglutinin (i.e. 75 μg per multidose vial). The composition may include trometamol, sodium chloride and polysorbate 80. The composition may include Tris-buffered saline and polysorbate 80. The vaccine may be administered intramuscularly e.g. to the deltoid or anterolateral thigh. The vaccine may be administered as two doses, given at least 3 weeks apart.

The invention also provides an unadjuvanted vaccine comprising a H1 subtype influenza A virus hemagglutinin which is more closely related to SEQ ID NO: 1 than to SEQ ID NO: 3 (e.g. from a A/California/7/2009 strain, such as X-179A). In a useful embodiment, this composition is a monovalent split virion inactivated vaccine in which the inactivated viruses were grown in eggs. The vaccine may be presented in a vial containing multiple doses (e.g. 10×0.5 ml unit dose with a thimerosal preservative, which may be present at 45 μg per 0.5 ml unit dose) or in syringes (one dose per syringe). The vaccine may be administered intramuscularly e.g. to the deltoid or anterolateral thigh. Each dose of vaccine may have 7.5, 15 or 30 μg of the H1 hemagglutinin. The vaccine may include a phosphate buffer.

The invention also provides a kit comprising (i) a first kit component comprising influenza A virus hemagglutinin, but not including a H1* hemagglutinin and (ii) a second kit component comprising an influenza A virus H1* hemagglutinin, provided that the second kit component does not comprise an oil-in-water emulsion adjuvant. Mixture of the two kit components gives a combined vaccine for administration to a subject. The second kit component is preferably monovalent i.e. it includes only one type of influenza hemagglutinin, namely the H1* hemagglutinin. The first kit component can be, for example: (a) a 3-valent vaccine composition including antigen from a H1N1 strain, a H3N2 strain, and one influenza B strain; (b) a 4-valent vaccine composition including antigen from a H1N1 strain, a H3N2 strain, a B/Victoria/2/87-like influenza B virus strain and a B/Yamagata/16/88-like influenza B virus strain; or (c) a monovalent vaccine composition comprising antigen from a H5N1 influenza A virus strain. In some embodiments, the first kit component includes an adjuvant, such as an oil-in-water emulsion.

The invention also provides a method for preparing an influenza vaccine, comprising a step of mixing a first kit component as defined in the preceding paragraph with a second kit component as defined in the preceding paragraph.

Vaccines mentioned in this section can usefully include a hemagglutinin comprising SEQ ID NO: 12.

Reassortant viruses

As mentioned above, the invention can use a reassortant influenza virus strain. Thus the invention provides an influenza A virus, wherein (a) the viral hemagglutinin gene encodes a hemagglutinin which is more closely related to SEQ ID NO: 1 than to SEQ ID NO: 3, and (b) at least one other viral gene is from the A/PR/8/34 influenza virus strain (A/Puerto Rico/8/34). Thus the virus may include at least one of segments NP, M, NS, PA, PB1 and/or PB2 from A/PR/8/34.

The invention also provides an influenza A virus, wherein (a) the viral hemagglutinin gene encodes a hemagglutinin which is more closely related to SEQ ID NO: 1 than to SEQ ID NO: 3 and (b) at least one other viral gene is from the AA/6/60 influenza virus strain (A/Ann Arbor/6/60). Thus the virus may include at least one of segments NP, M, NS, PA, PB1 and/or PB2 from AA/6/60. The AA/6/60 strain may be a cold-adapted AA/6/60 strain e.g. its PB1 may include one or more of K391E, E581G &/or A661T mutations in PB1, a N265S mutation in PB2, and/or a D34G mutation in NP [139].

The invention also provides an influenza A virus, wherein (a) the viral hemagglutinin gene encodes a hemagglutinin which is more closely related to SEQ ID NO: 1 than to SEQ ID NO: 3, and (b) at least one other viral gene is from the A/WSN/33 influenza virus strain. Thus the virus may include at least one of segments NP, M, NS, PA, PB1 and/or PB2 from A/WSN/33.

The invention also provides an influenza A virus, wherein (a) the viral hemagglutinin gene encodes a hemagglutinin protein which has at least k % sequence identity to SEQ ID NO: 1, where k is 85 or more e.g. 85, 88, 90, 92, 94, 95, 96, 97, 98, 99 or more (e.g. 100), and (b) at least one other viral gene is from the A/PR/8/34 influenza virus strain (A/Puerto Rico/8/34). Thus the virus may include at least one of segments NP, M, NS, PA, PB1 and/or PB2 from A/PR/8/34.

The invention also provides an influenza A virus, wherein (a) the viral hemagglutinin gene encodes a hemagglutinin protein which has at least k % sequence identity to SEQ ID NO: 1, where k is 85 or more e.g. 85, 88, 90, 92, 94, 95, 96, 97, 98, 99 or more (e.g. 100), and (b) at least one other viral gene is from the AA/6/60 influenza virus strain (A/Ann Arbor/6/60). Thus the virus may include at least one of segments NP, M, NS, PA, PB1 and/or PB2 from AA/6/60.

The invention also provides an influenza A virus, wherein (a) the viral hemagglutinin gene encodes a hemagglutinin protein which has at least k % sequence identity to SEQ ID NO: 1, where k is 85 or more e.g. 85, 88, 90, 92, 94, 95, 96, 97, 98, 99 or more (e.g. 100), and (b) at least one other viral gene is from the A/WSN/33 influenza virus strain. Thus the virus may include at least one of segments NP, M, NS, PA, PB1 and/or PB2 from A/WSN/33.

In these viruses, the viral neuraminidase gene may encode a neuraminidase protein which has at least j % sequence identity to SEQ ID NO: 4, where j is 75 or more e.g. 75, 80, 85, 88, 90, 92, 94, 95, 96, 97, 98, 99 or more (e.g. 100). In some embodiments, the neuraminidase is more closely related to SEQ ID NO: 4 than to SEQ ID NO: 5.

The eight segments of the influenza A virus genome encode (i) the PA subunit of the viral polymerase (ii) the PB1 subunit of the viral polymerase (iii) the PB2 subunit of the viral polymerase (iv) the viral nucleoprotein (v) the viral matrix proteins (vi) the viral NS1 and NS2 proteins (vii) hemagglutinin and (viii) neuraminidase. Preferred reassortants of the invention are 6:2 reassortants i.e. they include 6 segments from one strain (e.g. from A/PR/8/34, A/WSN/33 or AA/6/60) but the HA and NA segments from a different strain (e.g. as defined above by reference to SEQ ID NOs 1 and 4). In other embodiments there is a 7:1 reassortant with HA as defined above. In other embodiments the virus includes genes with three different origins, but with at least one segment (e.g. 1, 2, 3, 4, 5, 6) being from A/PR/8/34, A/WSN/33 and/or AA/6/60.

Viral segments from the A/PR/8/34, A/WSN/33 and AA/6/60 strains are widely available. Their sequences are available on the public databases e.g. GI:89779337, GI:89779334, GI:89779332, GI:89779320, GI:89779327, GI:89779325, GI:89779322, GI:89779329.

Reassortant viruses of the invention may have a H1* hemagglutinin with a binding preference for oligosaccharides with a Sia(α2,6)Gal terminal disaccharide compared to oligosaccharides with a Sia(α2,3)Gal terminal disaccharide.

A reassortant virus of the invention may have amino acid proline at residue 200 (numbered according to SEQ ID NO: 1). For example, it may encode hemagglutinin having sequence SEQ ID NO: 6. Other reassortants may encode hemagglutinin having sequence SEQ ID NO: 7 or SEQ ID NO: 9.

These viruses are particularly useful for preparing vaccines and can conveniently be prepared by reverse genetics. Vaccines including one or more A/PR/8/34 or A/WSN/33 viral genes may be used to prepare inactivated influenza vaccines. Vaccines including one or more AA/6/60 viral genes may be used to prepare live attenuated influenza vaccines.

The reassortant viruses of the invention can grow in MDCK cells, and the invention provides a method of preparing a virus, comprising steps of: (i) infecting a cell culture with a virus of the invention; (ii) culturing the cell culture from step (i) to produce further virus; and (iii) purifying virus obtained in step (ii). The cell culture in step (i) is preferably a MDCK cell culture, but other cells (ideally mammalian cells, such as PER.C6 cells) may be used as an alternative.

The invention also provides a host cell comprising one or more expression construct(s) for providing said reassortant strains. Thus the construct(s) may encode a viral hemagglutinin gene with a hemagglutinin which is more closely related to SEQ ID NO: 1 than to SEQ ID NO: 3. The construct(s) will additionally encode the other viral segments for the functional influenza genome, such as (i) at least one viral segment from the A/PR/8/34 influenza virus strain; (ii) at least one other viral segment from the AA/6/60 influenza virus strain; (iii) at least one other viral segment from the A/WSN/33 influenza virus strain; etc. The neuraminidase segment may encode a neuraminidase protein which has at least j % sequence identity to SEQ ID NO: 4, etc.

The invention also provides a construct or set of constructs encoding these reassortant strains e.g. when introduced into a host cell. Use of the construct(s) will provide an infectious influenza virus in a suitable reverse genetics host system. The constructs may be plasmids or non-plasmid vectors.

The invention also provides a process for RNA expression in a host cell, comprising the use of such construct(s). The invention also provides a method for producing a reassortant virus from such construct(s) and/or host cell(s).

NS1 mutant viruses

The invention also provides an influenza A virus, wherein (a) the viral hemagglutinin gene encodes a hemagglutinin which is more closely related to SEQ ID NO: 1 than to SEQ ID NO: 3, and (b) the viral genome does not encode a NS1 protein. The invention also provides an influenza A virus, wherein (a) the viral hemagglutinin gene encodes a hemagglutinin protein which has at least k % sequence identity to SEQ ID NO: 1, where k is 85 or more e.g. 85, 88, 90, 92, 94, 95, 96, 97, 98, 99 or more (e.g. 100), and (b) the viral genome does not encode a NS1 protein. NS1 knockout mutants are described in reference 140.

The invention also provides an influenza A virus, wherein (a) the viral hemagglutinin gene encodes a hemagglutinin which is more closely related to SEQ ID NO: 1 than to SEQ ID NO: 3, and (b) the viral genome encodes a truncated NS1 protein. The invention also provides an influenza A virus, wherein (a) the viral hemagglutinin gene encodes a hemagglutinin protein which has at least k % sequence identity to SEQ ID NO: 1, where k is 85 or more e.g. 85, 88, 90, 92, 94, 95, 96, 97, 98, 99 or more (e.g. 100), and (b) the viral genome encodes a truncated NS1 protein. Suitable truncations are known in the art (e.g. see references 141 & 142) and include truncations which leave only the first N-terminal 126 amino acids of NS1.

These NS1 -mutant virus strains are particularly suitable for preparing live attenuated vaccines.

The NS1 -mutant viruses ideally express PA, PB1, PB2, nucleoprotein, matrix, hemagglutinin and neuraminidase proteins.

Combination vaccines

In addition to the strain and vaccine combinations discussed above, the invention provides a multivalent immunogenic composition comprising (i) a H1 subtype influenza A virus hemagglutinin which is more closely related to SEQ ID NO: 1 than to SEQ ID NO: 3 and (ii) an influenza A virus hemagglutinin from 1, 2, 3 or 4 of hemagglutinin subtypes H2, H5, H7 and/or H9. Thus the composition may be H1-H2 bivalent, H1-H7 bivalent, H1-H2-H5 trivalent, H1-H5-H7-H9 tetravalent, H1-H2-H5-H7-H9 pentavalent, etc. At least two strains in the vaccine may share a common neuraminidase subtype e.g. a H1N1-H2N1 bivalent, H1N1-H2N2-H5N1 trivalent, etc.

Antibodies

The invention provides a monoclonal antibody which can bind to SEQ ID NO: 1 with higher affinity than to SEQ ID NO: 3. These monoclonal antibodies can be used in therapy.

Immunoassays

The invention provides an immunoassay for an influenza vaccine (e.g. a SRID assay) in which porcine anti-hemagglutinin antibodies are employed. These antibodies may be obtained from a pig following a swine flu infection. For instance, archived samples of swine sera may be used as a source of antibodies, thereby avoiding the delay typical for development of SRID reagents.

The invention also provides a gel including a porcine antiserum containing antibodies that recognize influenza hemagglutinin, and in particular which recognize the hemagglutinin of an influenza virus which can infect humans e.g. A/California/04/2009. The gel is suitable for performing a SRID assay e.g. it is an agarose gel.

The invention also provides an immunoassay for an influenza vaccine (e.g. a SRID assay) in which anti-hemagglutinin antibodies are employed, wherein the antibodies recognize the hemagglutinin of a swine influenza virus isolated in a year before 2009. The invention also provides a gel including an antiserum containing such antibodies. The gel is suitable for performing a SRID assay e.g. it is an agarose gel.

In some embodiments of the invention, HA concentration is not measured by SRID or by any other immunoassay, but is instead measured by an alternative assay e.g. by a chromatographic technique, such as by reverse phase high performance liquid chromatography (RP-HPLC).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g. as in Ph Eur general chapter 5.2.3.

Identity between polypeptide sequences is preferably determined by the Smith-Waterman homology search algorithm as implemented in the MPSRCH program (Oxford Molecular), using an affine gap search with parameters gap open penalty=12 and gap extension penalty=1.

MODES FOR CARRYING OUT THE INVENTION

Prime/boost regimen

A single dose of adjuvanted seasonal FLUAD™ vaccine is administered to subjects. Several weeks later (from 2-26 weeks later) they receive an unadjuvanted monovalent vaccine including hemagglutinin from A/California/04/2009 (SEQ ID NO: 1).

Reassortant strain

Mammalian cells were transfected with all 6 backbone segments of influenza A virus strain A/PR/8/34 and the two surface glycoprotein segments from an A/California/04/09 H1N1 strain in a reverse genetics system. An initial assay of culture fluid recovered from the transfected cells showed five positive results for rescued virus (FIG. 1A) and passaging of this material gave many more positive results (FIG. 1B).

To confirm that the observed viruses were true reassortants, strain-specific PCR primers were used to detect the HA, NA and PB1 genes. As shown in FIG. 2, the rescued virus (lanes '1') and the plasmid DNA used in the reverse genetics system (lanes '2') had the same size for all three genes, whereas PCR performed on water (lanes '3') showed no amplification.

Figure 3:
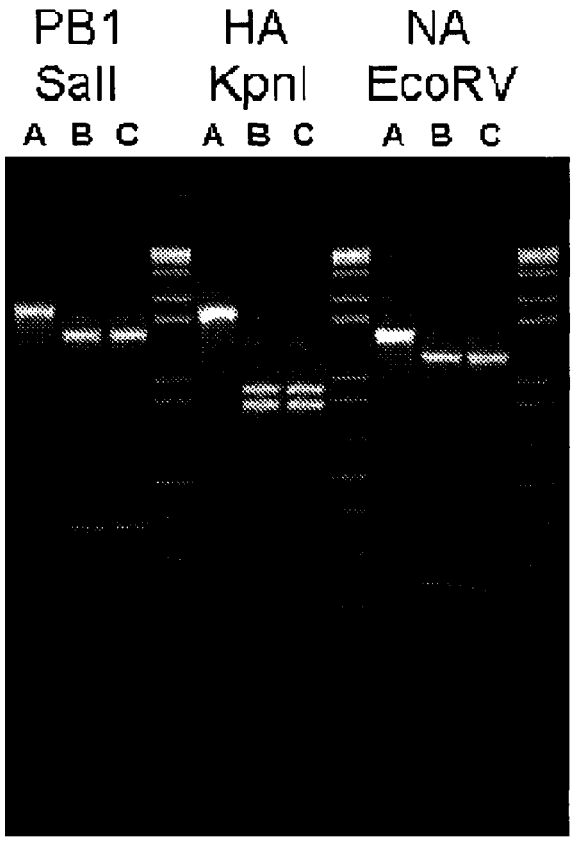
FIG. 3 shows results of a restriction digest.

A restriction digest was then performed on the PCR products. The PB1 gene in PR/8/34 includes a SalI site, whereas the PB1 gene in A/CA/04/09 does not. The HA gene in A/CA/04/09 includes a KpnI site, whereas the HA gene in PR/8/34 does not. The NA gene in A/CA/04/09 includes a EcoRVsite, whereas the NA gene in PR/8/34 does not. Thus these three restriction enzymes can distinguish between the two strains. As shown in FIG. 3 the PCR products (lanes 'A') were digested in all three cases, and the digestion products for the rescued reassortant (lanes 'B') and the original plasmid DNA (lanes 'C') were identical. Thus the virus produced by the reverse genetics system included the HA and NA genes from A/CA/04/09 and PB1 from A/PR/8/34, showing that it has been possible to produce an infectious reassortant virus.

Ferret study I

Reference 143 reports a ferret model for investigating influenza vaccines. Ferrets were primed with an adjuvanted (squalene-containing oil-in-water emulsion, MF59™; not an embodiment of the invention) or unadjuvanted seasonal vaccine, or with PBS. Three weeks later (day 21) these ferrets received a booster dose of adjuvanted or unadjuvanted trivalent seasonal or a monovalent pandemic ('H1N1sw') vaccine, or PBS. Eight animal groups A to H were used in total:

| Group | A | B | C | D | K | F | G | H |
|---|---|---|---|---|---|---|---|---|
| Prime | S,A | S,A | S,A | S | Ss | S | PBS | PBS |
| Boost | S,A | sw | sw,A | S | sw | sw,A | sw,A | PBS |

S = seasonal, sw = swine, A = adjuvanted

At day 49 ferrets were then challenged with a H1N1sw strain ($10^6$ $TCID_{50}$) and lung pathology was assessed in each group. Unlike seasonal H1N1, which infects only nose and trachea, the H1N1sw virus also infects the lungs. The H1N1sw virus is not lethal for the ferrets.

The average % of affected lung parenchyma were:

| Group | A | B | C | D | E | F | G | H |
|---|---|---|---|---|---|---|---|---|
| % | 13.3 | 6.7 | 3.3 | 15.8 | 7.5 | 6.7 | 3 3 | 48.3 |

Thus, compared to the PBS group, all ferrets previously primed with either adjuvanted or unadjuvanted seasonal vaccine and then boosted with either the homologous seasonal or with H1N1sw had an important reduction in the lung pathology.

Figure 6:
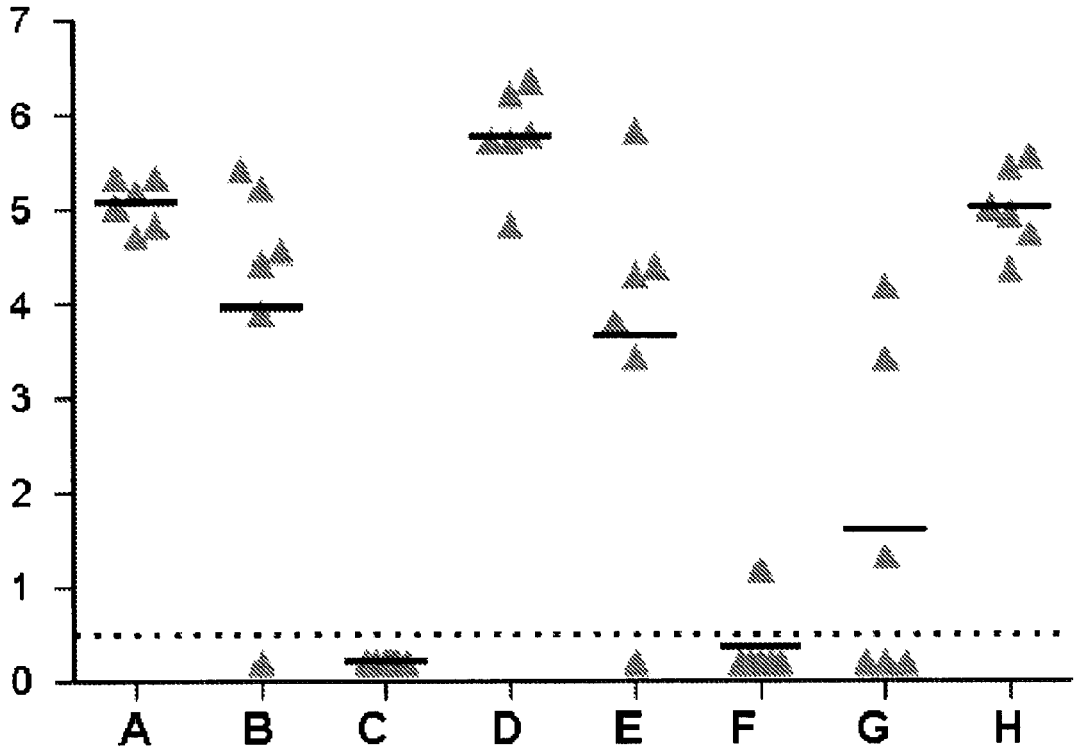
FIG. 6 shows lung viral load in ferrets immunized with various prime/boost regimens. Animal groups A to H are described below. The y-axis shows $Log_{10}TCID_{50}$/gr.

Lung viral load was also assessed and results are shown in FIG. 6. As compared to PBS, one dose of adjuvanted H1N1sw vaccine reduced lung viral load by 2 to 3 logs (compare groups G & H). The viral load in the lungs was reduced to almost undetectable levels (group F) if the H1N1sw vaccination was preceded by administration of an unadjuvanted seasonal influenza vaccine.

Figure 7:
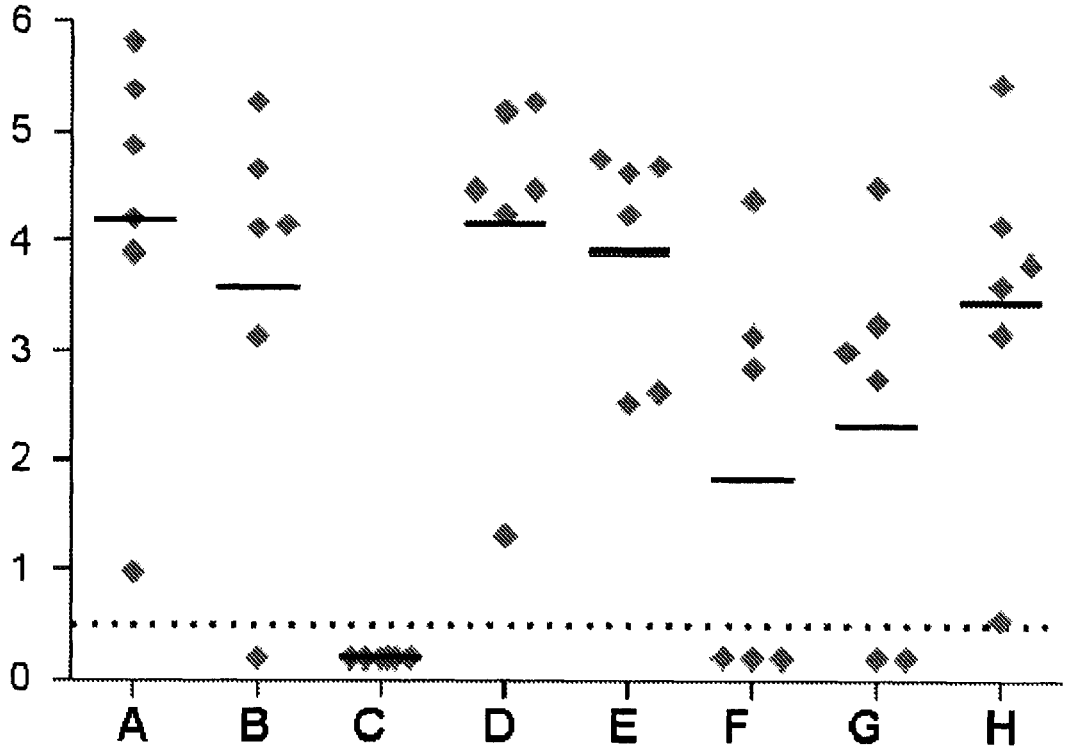
FIG. 7 shows nasal viral load in the same ferrets and the y-axis shows $log_{10}$ CDU.

Viral load was also assessed from nasal swabs (FIG. 7). Similar results were found in throat swabs.

Figure 8:
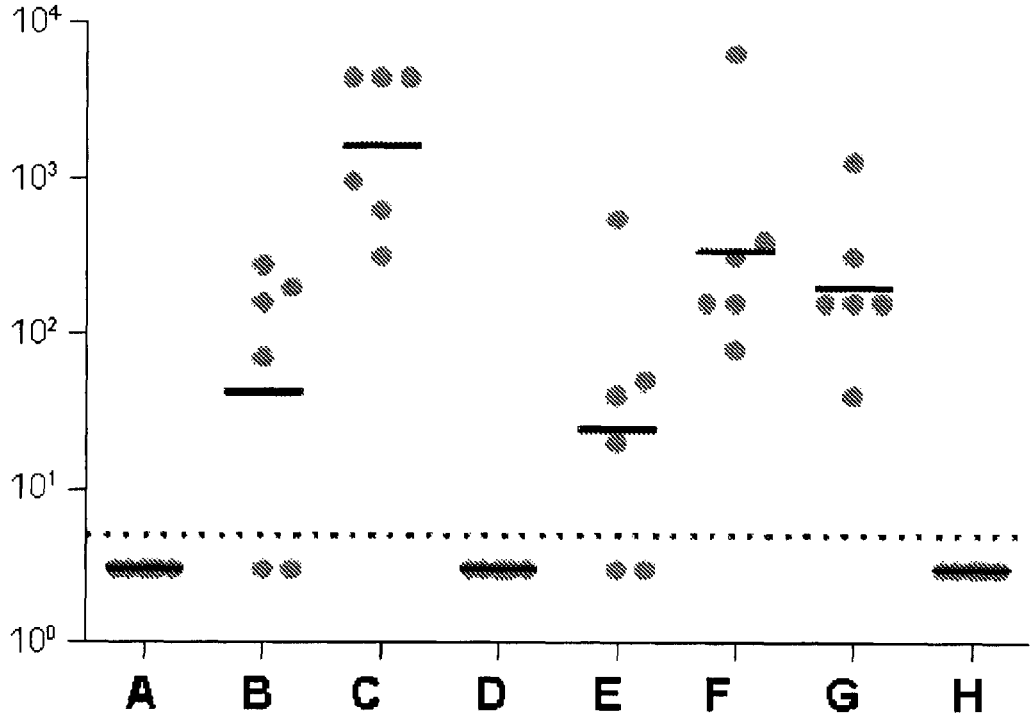
FIG. 8 shows HI titers in the same ferrets.
Figure 9:
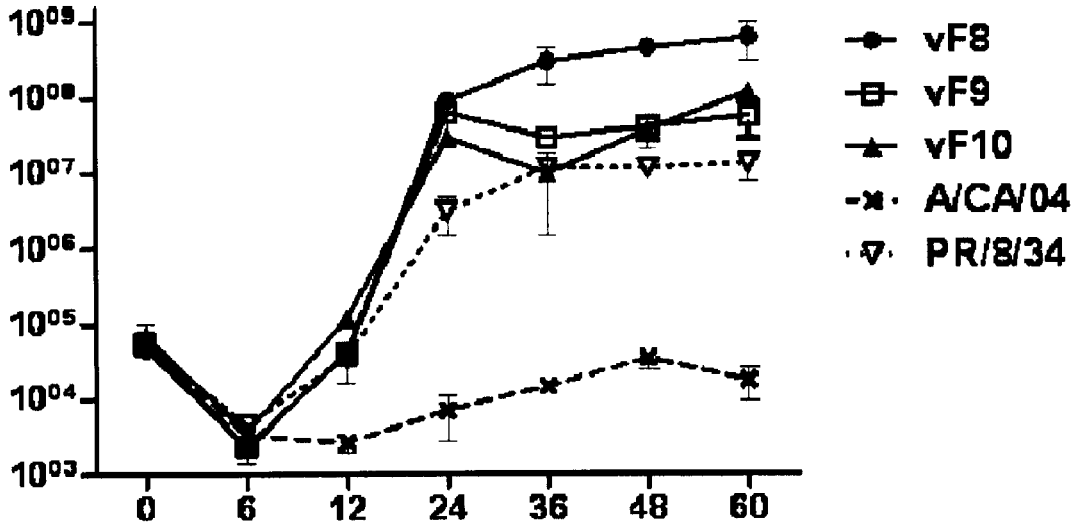
FIGS. 9-12 show data for the F8, F9 and F10 variants obtained during reverse genetics work, compared to A/CA/04/09 and A/PR/8/34.
Figure 10:
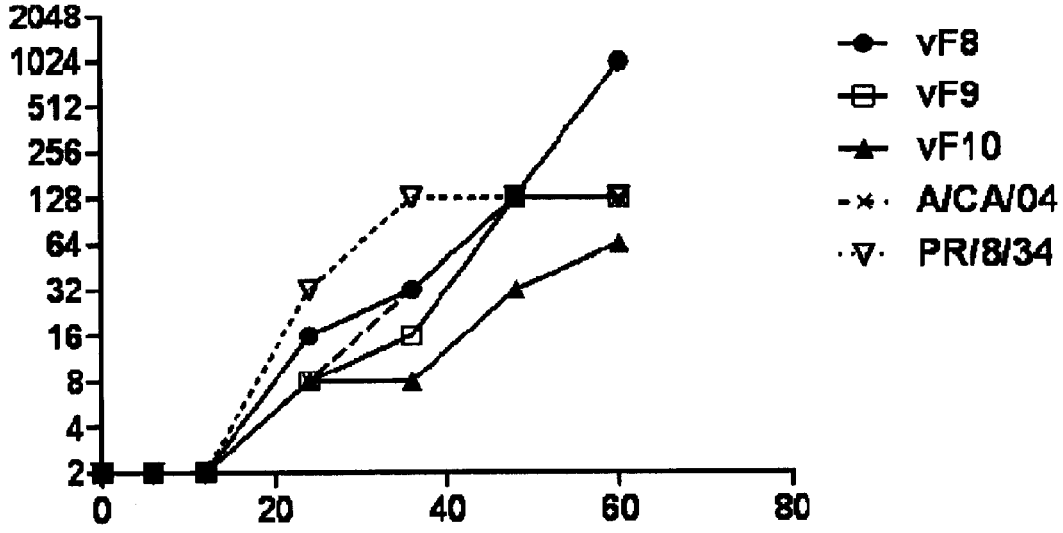

HI antibody responses were also measured at day 49 (FIG. 8). One dose of adjuvanted H1N1sw vaccine was more immunogenic than unadjuvanted H1N1sw vaccine. HI titers against H1N1sw virus increased by at least 1 log in ferrets previously immunized with adjuvanted seasonal vaccine.

HI antibody responses against seasonal H1N1 and H3N2 seasonal strains were also assessed. Antibodies which cross-react between seasonal H1N1 and H1N1sw were not detected by HI.

Thus one dose of adjuvanted H1N1sw vaccine was more immunogenic and more efficacious than unadjuvanted vaccine, measured by viral loads in lungs, nose, and throat. Both immunogenicity and efficacy were enhanced by previous immunization with seasonal influenza vaccine, and this effect was better if the seasonal vaccine was adjuvanted. This enhancement of immunogenicity and efficacy does not appear to be due to antibodies cross-reacting (by HI) between seasonal H1N1 and H1N1sw.

These results can explain why elderly people might be better protected against H1N1sw virus despite little cross-reactivity of antibodies. They can also explain the preliminary results of clinical trials showing good response after one single dose in healthy adults, as this effect could be due to previous immunological experience with seasonal viruses (via natural infection or vaccination), despite little or no cross-reactivity of antibodies. The results also imply that better H1N1sw protection is achieved in the presence of an adjuvant and if a patient has previously been immunized with adjuvanted seasonal vaccine. The data suggest that immunologically naive individuals (e.g. children) and immunologically frail individuals may require more than one dose of adjuvanted H1N1sw vaccine for optimal and sustained protection even though a single dose can still be clinically useful.

Further details of this ferret study are in reference 144.

Mouse study I

In unprimed mice, without any prior exposures to flu antigens, a single dose of emulsion-adjuvanted H1N1sw vaccine (not an embodiment of the invention) gives HI titers associated with protection in humans. Without the adjuvant, two doses were required to reach this titer.

Vaccines were prepared from H1N1sw A/California/07/2009 H1N1-like viruses grown in eggs. Vaccines were either unadjuvanted or were adjuvanted with an oil-in-water emulsion comprising squalene (MF59™). Vaccines were standardized by SRID with a HA dose of either 0.5 μg or 1 μg. Balb/c mice aged 6-7 weeks were immunized intramuscularly on day 0 with phosphate buffered saline, with 0.5 or 1.0 μg (HA content) of antigen alone, or with 0.5 μg of antigen with 50 μl of adjuvant. Dose volume was 100 μl. Sera were obtained on day 13. Mice were boosted with a second dose, matching the first, on day 14. Sera were again collected on day 21. Sera were assayed by hemagglutination inhibition (HI) using inactivated whole virus for antigen and turkey red blood cells.

Figure 4:
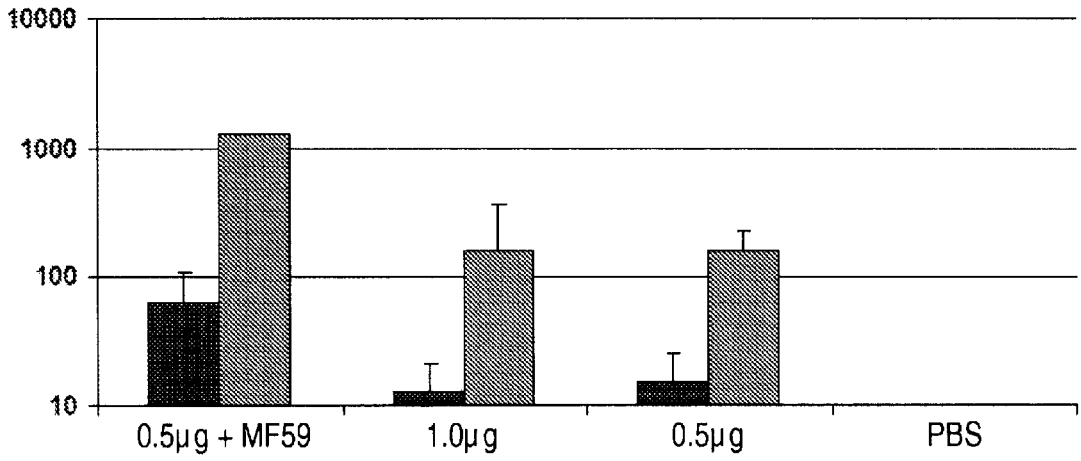
FIG. 4 shows H1 titers obtained after immunization with H1N1sw antigen either unadjuvanted (0.5 or 1 μg HA dose) or adjuvanted with MF59 (0.5 μg). A PBS control was also used. The black bars show titers after one immunization; the grey bars show titers after two immunizations.

A single immunization with 0.5 μg adjuvanted antigen elicited an average functional antibody (HI) titer of 1:63 in serum obtained two weeks after immunization (FIG. 4). A HI titer of 1:40 or more is associated with protection of humans from seasonal influenza [145]. A second immunization with adjuvanted vaccine two weeks later increased the average HI titer to 1:1280 in serum obtained one week after the boost. A single immunization with antigen without adjuvant did not elicit significant HI titers, but a second immunization two weeks later elicited a HI titer of 1:160. There was no significant difference in titers elicited by immunization with 0.5 or 1.0 μg of unadjuvanted antigen.

These data are consistent with results of human immunization with vaccines against other potential pandemic influenza strains. Without adjuvant, vaccines against H5 avian influenza strains elicit low antibody titers; MF59 greatly increases the rapidity, titer, and breadth of the elicited antibodies [146,147]. During a much smaller human outbreak of swine origin influenza in 1976, adjuvanted vaccines were not available. A single dose of the 1976 vaccines elicited low antibody titers in young people, but significantly higher titers in older individuals, probably because older subjects had experienced more priming influenza infections or immunizations [148].

Mouse study II

Mice primed with seasonal H1N1 (A/Brisbane/59/2007; 0.2 μg HA dose) monovalent vaccine (with or without MF59 adjuvant) were boosted twice (days 36 and 66) with the same vaccine or with equivalent monovalent vaccines (again, with or without MF59 adjuvant) prepared from pandemic H1N1sw strains (A/California/04/2009 hemagglutinins).

Figure 5:
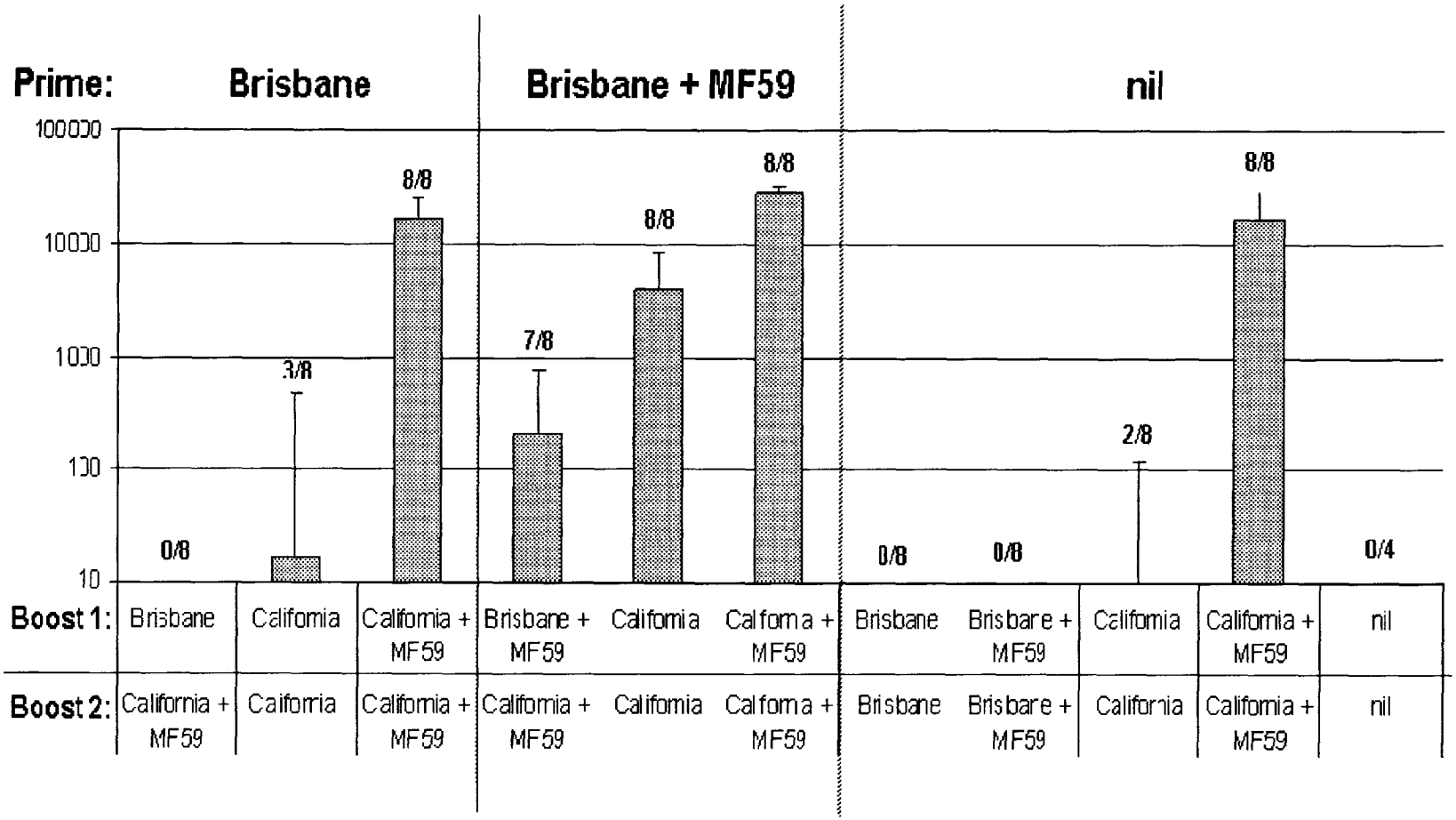
FIG. 5 shows IgG serum antibody titers (ELISA) after two H1N1sw boosting doses in mice primed with seasonal H1N1 (Brisbane). The priming and boosting strains and adjuvanting are indicated.

ELISA analysis of the immune responses (FIG. 5) suggests that prior seasonal adjuvanted vaccination effectively primed the mice for a higher titer response to the H1N1sw vaccine, and this priming was especially important if the H1N1sw vaccine was unadjuvanted. In unprimed mice or mice primed with unadjuvanted seasonal H1N1, a high titer response was seen only if the H1N1sw vaccine was adjuvanted.

Thus adjuvanting of the H1N1sw vaccine seems to be important for a robust immune response. Moreover, adjuvanting seems to be important for allowing the seasonal vaccine to prime for a robust antibody response to the pandemic vaccine.

In summary, immunization with two doses of unadjuvanted pandemic vaccine elicited little functional antibody in un-primed mice or in mice primed with unadjuvanted seasonal vaccine. In mice primed with adjuvanted seasonal vaccine, however, two doses of unadjuvanted pandemic vaccine gave a good response. Mice responded robustly to two doses of adjuvanted pandemic vaccine regardless of whether they had been primed. Although adjuvanted seasonal vaccines may not efficiently elicit antibodies against the pandemic strain, therefore, they may prime for a higher titer response to pandemic vaccines.

Mouse study III

Three groups of 40 6-week-old female BALB/c mice received a single i.m. injection of a trivalent seasonal vaccine, from either the 2005/06 season or the 2009/10 season (both northern hemisphere). Influenza-naive control mice received PBS. The vaccines were administered at 1/10th the human dose (1.5 μg HA per strain) on day 0. On day 40 mice were divided into four subgroups of 10 animals each and were re-vaccinated with a monovalent inactivated H1N1sw vaccine. The four groups received a high or low dose (3 μg HA or 0.3 μg HA), with or without a submicron oil-in-water emulsion adjuvant comprising squalene in combination with sorbitan oleate, polyoxyethylene cetostearyl ether and mannitol. All animals then received a second H1N1sw dose at day 61. The presence of HI antibodies against the seasonal and pandemic H1N1 strains was assessed at days 40, 61, 75 and 102. Full details of this mouse study are given in reference 149.

The results confirmed that a single injection of the H1N1sw vaccine was sufficient to induce HI antibody responses to protective levels, with or without adjuvant. The HI antibody titer (GMT) against the H1N1sw strain was >40 in all groups except for the group of naïve mice immunized with 0.3 μg HA of unadjuvanted vaccine.

Antibodies elicited by previous seasonal influenza vaccination did not cross-react with the H1N1sw strain, but priming with seasonal influenza vaccines did result in higher antibody responses to non-adjuvanted H1N1sw vaccine. In contrast, previous seasonal immunization did not appear to influence the immunogenicity of the adjuvanted H1N1sw vaccine in mice, likely due to a strong primary response induced by the adjuvanted vaccine in these groups.

Mouse study IV

VLPs were prepared from recombinant H1N1sw HA expressed in Sf9 insect cells. The VLPs contained ~0.1 mg HA per mg of total VLP protein. Female BALB/c mice were immunized i.m. with 0.1 mg or 10 mg (total protein) VLPs (no adjuvant) and used in challenge studies. Full details of the study are reported in reference 150. A single intramuscular vaccination with VLPs provided complete protection against lethal challenge with the A/California/04/2009 virus, even at a low dose. Thus VLP vaccination can provide highly effective protection.

Mouse study V

H1N1sw virus was grown in Vero cell culture. Viruses were harvested, double-inactivated and purified. Female CD1 mice were immunized s.c. with inactivated viruses diluted to between 0.0012 μg and 3.75 μg HA. Full details of the study are reported in reference 151. The unadjuvanted whole virus vaccine was immunogenic at low doses and was protective in both active and passive transfer challenge studies.

Human study I (Leicester, UK)

As reported in reference 152 monovalent surface antigen vaccines were prepared from an A/California/7/2009 H1N1sw strain. The vaccine strain had HA, NA and PB1 gene segments from A/California/7/2001 H1N1sw and the other five segments were from A/PR8/8/34. Virus was grown in MDCK cells. Viruses and antigens were prepared using the process used to make the trivalent OPTAFLU™ product [153]. Two vaccines were prepared: an adjuvanted vaccine (not an embodiment of the invention) with 7.5 μg HA and the MF59 oil-in-water emulsion comprising submicron squalene droplets; and an unadjuvanted vaccine with 15 μg HA in buffer. All vaccines had a 0.5 ml volume. A half-dose of the adjuvanted vaccine was used for some subjects (i.e. with a 0.25 ml volume). HA content in the final vaccine was determined by means of reverse-phase HPLC because SRID reagents were unavailable.

175 subjects were split into seven groups. Subjects received either one dose (day 0) or two identical doses (day 0; day 7, 14 or 21). The seven groups A to G were as follows (doses; adj=adjuvanted):

| Group | A | B | C | D | E | F | G |
|---|---|---|---|---|---|---|---|
| Dose 1 | 15 μg, adj | 7.5μg, adj | 7.5 μg, adj | 7.5 μg, adj | 3.75 ug, adj | 7.5 μg | 15 μg |
| Dose 2 | — | Day 7 | Day 14-1 | Day 21 | Day 21 | Day 21 | Day 21 |

Immunogenicity was assessed at days 0, 14 and 21. An interim assessment measured immunogenicity immediately prior to administration of the day 21 dose. Thus groups A to C had completed their regimens whereas group D had received only a single 7.5 μg adjuvanted dose. Groups E to G were not assessed at this interim stage. Antibody responses by were assessed by hemagglutination (HI) assay, as geometric mean titers (GMT), geometric mean ratios, seroconversion (%) and seroprotection (%). Antibody responses were also assessed by microneutralization (MN) as GMTs, proportion of subjects with a titer ≧40 (%) or seroconversion.

Antibody responses by HI in the interim assessment were as follows:

| Group | D | A | B | C |
|---|---|---|---|---|
| | | Day 0 | | |
| GMT | 6.2 | 6.0 | 4.8 | 6.6 |
| Scroprotection | 12 | 8 | 4 | 12 |
| | | Day 14 | | |
| GMT | 195.6 | 294.8 | 416.5 | 155.8 |
| GM ratio | 31.7 | 492 | 86.7 | 23.7 |
| Seroconversion | 79 | 91 | 96 | 68 |
| Seroprotection | 83 | 96 | 100 | 72 |
| | | Day 21 | | |
| GMT | 172.5 | 256.1 | 282.9 | 288.7 |
| GM ratio | 27.9 | 42.7 | 58.9 | 43.8 |
| Seroconversion | 76 | 88 | 92 | 88 |
| Seroprotection | 80 | 92 | 96 | 92 |

Antibody responses by MN in the interim assessment were as follows:

| | D | A | B | C |
|---|---|---|---|---|
| | | Day 0 | | |
| GMT | 13.4 | 10.4 | 9.8 | 13.1 |
| Ab titer ≧40 | 20 | 12 | 16 | 16 |
| | | Day 14 | | |
| GMT | 353.3 | 606.5 | 502 2 | 285.4 |
| Seroconversion | 83 | 91 | 96 | 84 |
| Ab titer ≧40 | 100 | 100 | 100 | 92 |
| | | Day 21 | | |
| GMT | 348.2 | 582.8 | 448.9 | 407.2 |
| Seroconversion | 92 | 92 | 96 | 96 |
| Ab titer ≧40 | 100 | 100 | 100 | 100 |

Pre-immunization antibodies were detected by HI assay (titer >1:8) and MN assay (titer >1:10) in 14% and 39% of subjects, respectively, with this frequency unrelated to age or to previous receipt of seasonal vaccine. On day 14, geometric mean titers (GMTs), as measured with the use of HI and MN assays were higher in subjects who received two 7.5 μg adjuvanted doses as compared to those who had received only one dose (compare groups A to C against group D) but there was no significant difference in titer among the groups. On day 21, there was no significant difference in titer among subjects who had received one dose or two doses. All subjects had MN antibody at a titer exceeding 1:40 by day 21.

Thus immune responses at the interim stage were consistent, with seroprotection against the 2009 H1N1sw virus within 2 weeks after administration of a single dose of the adjuvanted vaccine. One or two doses of the adjuvanted vaccine containing 7.5 μg of HA administered on various schedules elicited robust antibody titers. Although a double dose (15 μg HA) gave higher antibody levels than one dose, the seroprotective titer was attained in at least 80% of subjects in every group.

Human study II (Australia)

As reported in reference 154 an unadjuvanted monovalent split vaccine was prepared from an A/California/7/2009 H1N1sw strain. The vaccine was prepared in embryonated chicken eggs with the same standard techniques that are used for the production of CSL's seasonal trivalent inactivated vaccine [155]. Two different vaccines were used: one with a 15 μg HA dose (0.25 ml volume) and another with a 30 μg HA dose (0.5 ml volume). A total of 240 adults aged 18-64 were vaccinated intramuscularly into the deltoid. 45% of subjects had received the 2009 southern hemisphere seasonal vaccine.

A single 15 μg or 30 μg dose of the H1N1 vaccine produced a robust immune response in a majority of subjects. Post-vaccination titers of 1:40 or more (HI assay) were observed in 96.7% of recipients of the 15 μg dose and in 93.3% of the recipients of the 30 μg dose. Seroconversion or a significant increase in titer on HI assay occurred in 74.2% of subjects, and the effect was similar between the two doses groups. After vaccination there was a substantial rise in GMTs with no significant differences in factor increases between the two doses. Age-related differences were seen, however, and subjects who were ≧50 years old had a numerically lower factor increase in GMTs. This age-related effect was reflected in all measures of immunogenicity. No deaths, serious adverse events, or adverse events of special interest were reported.

HI results after a single dose were as follows (see Table 2 of reference 154 for more details):

| | 15 μg | | | 30 μg | | |
|---|---|---|---|---|---|---|
| | 18-49 y.o. | 50-64 y.o. | All ages | 18-49 y.o. | 50-64 y.o. | All ages |
| Subjects with HI titer ≧1:40 | 100% | 93 5% | 96.7% | 98.4% | 87.9% | 93.3% |

-continued

| | 15 μg | | | 30 μg | | |
|---|---|---|---|---|---|---|
| | 18-49 y.o. | 50-64 y.o. | All ages | 18-49 y.o. | 50-64 y.o. | All ages |
| GMT | 306.9 | 157.0 | 217 1 | 513.7 | 174.0 | 304.4 |
| Pre:post Increase in GMT | 14.3x | 8.1x | 10.7x | 25.8x | 13.2x | 18.6x |

Thus a single 15 μg dose of unadjuvanted H1N1sw vaccine resulted in titers of 1:40 or more by HI assay in >95% of adult subjects i.e. two doses of vaccine were not required for a robust immune response. This effect was seen even in subjects with no measurable antibodies at baseline.

Human study III

A monovalent H1N1sw vaccine was given to human volunteers either with or without simultaneous administration of a trivalent 2009/10 seasonal vaccine. Both vaccines were inactivated whole virion vaccines with an aluminum phosphate adjuvant. The seasonal vaccine included 15 μg HA per strain, but the H1N1sw vaccine included only 6 μg HA. Full details of this human study are given in reference 156.

There were no observed clinically significant changes in the physical condition of the volunteers, and no vaccine-related moderate or any serious adverse events. Side effects were rare and mild, and no medical intervention was necessary. Simultaneous administration of the seasonal vaccine with the H1N1sw vaccine was safe and immunogenic. Relevant licensing parameters against each of the four vaccine strains, achieved using the monovalent H1N1sw vaccine alone or in combination with the seasonal vaccine, were as follows:

| | | H1Nlsw | | H1N1 | | H3N2 | | B | |
|---|---|---|---|---|---|---|---|---|---|
| | Age | Mono | Combo | Mono | Combo | Mono | Combo | Mono | Combo |
| GMT ratio | 18-60 | 9.1 | 7.6 | 1.2 | 3.7 | 1.1 | 3.8 | 1.0 | 3.8 |
| | >60 | 6.3 | 8.0 | 1.2 | 2.7 | 1.2 | 2.8 | 1.1 | 3.1 |
| Seroconversion | 18-60 | 74.3% | 76.8% | 0 | 67.7% | 0 | 70.7% | 0 | 59.6% |
| | >60 | 61.3% | 81.8% | 0 | 40.3% | 0 | 49.4% | 0 | 53.3 |
| Seropositivity | 18-60 | 74.3% | 76.8% | 25.7% | 76.8% | 26.7% | 78.8% | 40.6% | 75.8% |
| | >60 | 61.3% | 81.8% | 17.3% | 68.8% | 17.3% | 70.1% | 24.0% | 75.3% |

Thus the H1N1sw vaccine fulfilled all international licensing criteria in adult (203 subjects, 18-60 years old) and elderly (152 subjects, >60 years old) age groups even after a single dose, and even when given at the same time as a seasonal influenza vaccine.

Human study IV

A monovalent inactivated split vaccine from a H1N1sw strain was given to human adult volunteers (18-60 years old). Patients received either an adjuvanted or unadjuvanted vaccine. The adjuvanted vaccine (not an embodiment of the invention) had 5.25 μg HA with a submicron oil-in-water emulsion comprising squalene (AS03); the unadjuvanted vaccine had 21 μg HA. Vaccines were administered on days 0 and 21. HI titers against A/California/7/2009 were assessed on these days, as well as seroconversion and seroprotection. Full details of this human study are given in reference 157.

The vaccine was well tolerated, and immunogenicity results were as follows:

| | | Adjuvanted | Unadjuvanted |
|---|---|---|---|
| Day 0 | GMT | 10.6 | 11.7 |
| | Seroprotection | 12.5% | 13.1% |
| Day 21 | GMT (fold rise) | 541.7 (51.3) | 530.5(45.3) |
| | Seroprotection | 98.2% | 98.4% |
| | Seroconversion | 98.2% | 95.1% |

Thus the adjuvanted and unadjuvanted vaccines were both immunogenic in adults, and a single dose of either 5.25 μg HA (adjuvanted) or 21 μg HA (non-adjuvanted) was enough to satisfy licensure criteria.

Human study V

Two multicenter randomized, dose-ranging studies evaluated non-adjuvanted and adjuvanted (with MF59; not an embodiment of the invention) and egg-derived and culture-derived monovalent H1N1sw vaccines in healthy children 6 months to 17 years of age. The aim was to identify the preferred vaccine formulation (with or without adjuvant), dosage and schedule (one or two administrations) in healthy children and adolescents.

At enrolment, subjects were (i) stratified into four age cohorts i.e. 9-17 yr., 3-8 yr., 12-35 mo. and 6-11 mo; and (ii) randomized into three vaccine groups given 3.75 μg HA+½ dose MF59, 7.5 μg HA+full dose MF59 or 15 μg HA unadjuvanted. Children aged 9-17 yr and infants aged 6-11 mo received only the adjuvanted vaccines. Subjects received two vaccinations 21 days apart. Vaccines were prepared either in eggs or in MDCK cell culture (suspension culture).

Immunogenicity was determined 21 days after each vaccination by hemagglutination inhibition (HI). Geometric mean HI titer (GMT) and geometric mean ratio (GMR) of post-/pre-vaccination HI titers were calculated. Seroconversion rate was also assessed i.e. % of subjects with post-vaccination HI ≧1:40 and negative at baseline (HI <1:10), or a minimum 4-fold increase in HI titre for subjects positive at baseline (HI≧1:10). Seroprotection rate (SP) was also assessed i.e. ˆ of subjects with a HI titer ≧1:40

Interim presents were obtained from subjects 3-8 and 9-17 years of age (388 subjects who received cell-derived vaccine, and 403 subjects who received egg-derived vaccine).

GMT and GMR values in the subjects receiving the cell-derived vaccine were as follows:

| | | 3.75 μg HA ½ dose MF59 | 7.5 μg HA Full MK59 | 15 μg HA no adjuvant |
|---|---|---|---|---|
| | 9-17 years | N = 81 | N = 81 | N = NA |
| GMT | Day 1 | 6.38 (5.35-7.61) | 5.91 (4.97-7.02) | — |
| | Day 22 | 79 (55-114) | 132 (92-187) | — |
| | Day 43 | 346 (283-424) | 525 (431-640) | — |
| GMR | Day 22:1 | 12 (8.68-18) | 22 (16-32) | — |
| | Day 43:1 | 54 (42-70) | 89 (70-113) | |
| | 3-8 years | N = 86 | N = 86 | N = 44 |
| GMT | Day 1 | 5.64 (4.83-6.6) | 5.74 (4.92-6.69) | 5.24 (4.3-6.39) |
| | Day 22 | 44 (32-62) | 55 (40-77) N = 85 | 21 (14-32) |
| | Day 43 | 100 (317-506) | 547 (434-689) | 122 (90-164) |
| GMR | Day 22:1 | 7.88 (5.61-11) | 9.64 (6.89-13) | 3.97 (2.58-6.1) |
| | Day 43:1 | 71 (52-97) | 95 (70-129) | 23 (15-34) |

GMT and GMR values in the subjects receiving the egg-derived vaccine were as follows:

| | | 3.75 μg HA ½ dose MF59 | 7.5 μg HA Full MF59 | 15 μg HA no adjuvant |
|---|---|---|---|---|
| | 9-17 years | N = 94 | N = 94 | N = NA |
| GMT | Day 1 | 12 (8.62-16) | 12 (8-88-17) | — |
| | Day 22 | 503 (348-729) | 718(496-1041) | — |
| | Day 43 | 698 (544-896) | 969 (755-1243) | — |
| GMR | Day 22:1 | 43 (28-66) | 59 (38-91) | — |
| | Day 43:1 | 59 (40-87) | 30 (54-118) | — |
| | 3-8 years | N = 87 | N = 85 | N = 43 |
| GMT | Day 1 | 8.23 (5.78-12) | 963 (6.67-14) | 11 (6.92-16) |
| | Day 22 | 212(139-324) | 281 (181-435) | 88(53-146) |
| | Day 43 | 622 (433-893) N = 77 | 658 (452-960) N = 74 | 146 (95-225) N = 37 |
| GMR | Day 22:1 | 26(17-38) | 29(19-44) | 8.39 (5.25-13) |
| | Day 43:1 | 80 (50-127) N = 77 | 72 (45-117) N = 74 | 16 (9-27) N = 37 |

The adjuvanted vaccines in the two studies had SP rates ≧70% 3 weeks after the first and the second vaccination in the 9-17 and 3-8 year age cohorts. Unadjuvanted vaccines in the two studies achieved SP rates ≧70% in 3-8 year age cohorts 3 weeks after the second vaccine dose. All vaccines in both age cohorts (3-17 years) had SC rates ≧40% three weeks after the first and the second vaccination in both studies. GMTs increased strongly three weeks after each dose, and all vaccines in both cohorts had GMRs ≧2.5.

The adjuvanted egg-derived (FOCETRIA™) and cell culture-derived (CELTURA™) vaccines (not embodiments of the invention) induced rapid, strong immune responses at a lower HA dose than a vaccine without adjuvant. The immunogenicity of all adjuvanted vaccines met European regulatory (EMA) pandemic influenza vaccine criteria (>70% subjects with HI titre ≧1:40; seroconversion >40% and GMR >2.5) following a single dose.

Human study VI (Costa Rica)

This study aimed to determine the safety and antibody responses after administration of adjuvanted (with MF59; not an embodiment of the invention) or unadjuvanted H1N1sw vaccines in a pediatric population. The vaccines were prepared from egg-grown virus. Subjects were divided in two age groups (children ages 3-8 yrs and adolescents ages 9 to 17 yrs) and were randomized to (a) one 7.5 μg dose of adjuvanted vaccine, which is not an embodiment of the invention, (b) one 15 μg unadjuvanted dose, or (c) 30 μg unadjuvanted dose (2×15 μg doses). Three weeks later, subjects received an MF59-adjuvanted vaccine with 7.5 μg of H5N1 hemagglutinin (surface antigen vaccine, egg-derived). Blood samples for serologic testing were collected on day 1 (immunization), day 22, day 29 and day 43. Antibody titers against the H1N1 vaccine antigen were evaluated by haemagglutination inhibition (HI). Geometric mean titers (GMTs) of anti-haemagglutination inhibition antibody, seroconversion (SC) rates and percentage of subjects with HI titer ≧1:40 were calculated. SC rates and HI titer ≧1:40 were compared to available Center for Biologics Evaluation and Research (CBER) regulatory criteria. The lower bound of the 95% CI for SC rate should be ≧40%. The lower bound of the 95% CI for percentage with HI titer ≧1:40 should be ≧70%.

A total of 194 children and 196 adolescents were enrolled. After the first dose (day 22), 93% of children given the 7.5 μg adjuvanted vaccine achieved HI titer ≧1:40, compared with 72-74% of those given unadjuvanted vaccines. The SC rate (day 22) for the adjuvanted vaccine in children ages 3-8 years (91%) was higher than for non-adjuvanted vaccines (71-72%). By day 29, all subjects given 7.5 μg of adjuvanted vaccine achieved HI titer ≧1:40; all vaccines met the CBER criteria. Seroconversion rates following the second vaccine dose ranged from 83-95% across all study groups. GMTs rose after each vaccination, but more strongly in subjects given 7.5 μg adjuvanted vaccine, particularly in children.

All three H1N1 vaccines generated high HI antibody responses in a pediatric population within 2 doses of vaccine, but after a single dose only the adjuvanted vaccine achieved HI antibody responses meeting CBER immunogenicity criteria.

Human study VII (USA)

A dose-ranging study was performed to evaluate the optimal dose in the pediatric population of a monovalent H1N1sw vaccine with oil-in-water adjuvant MF59 (not an embodiment of the invention) or unadjuvanted. A total of 1357 healthy children, 3 to <9 years of age, were enrolled. Children were randomized equally to eight groups and given intramuscular vaccine injections on Day 1 and Day 22. Vaccines were formulated as 3.75, 7.5, 15 or 30 μg HA with or without a full or half dose of MF59.

Immunogenicity (HI assay) according to CBER criteria [HI titre ≧1:40 (95% CI lower bound ≧70%) and seroconversion rate (95% CI lower bound ≧40%)] was evaluated on Day 22 and 43. Seroconversion was defined as a prevaccination HI titre <1:10 and post-vaccination titre ≧1:40, or a pre-vaccination HI titre ≧1:10 and ≧4-fold rise in post-vaccination titre. HI antibody responses were expressed as geometric mean titers (GMTs) and geometric mean ratio (GMRs) of the post- to pre-vaccination titer. Pairwise comparisons of GMT ratios between each group were performed and 95% CI were assessed against a noninferiority margin of 0.5, and, subsequently, 0.67. Differences between vaccine groups were assumed to be statistically significant if the 2-sided 95% CI around the GMT ratio did not contain 1, showing either statistically significant superiority or inferiority.

GMT and GMR results were as follows:

| Antigen | 3.75 | 7.5 | 7.5 | 7.5 | 15 | 15 | 15 | 30 |
|---|---|---|---|---|---|---|---|---|
| Adjuvant | ½ | 0 | 1/2 | 1 | 0 | ½ | 1 | 0 |
| Subjects | 152 | 157 | 156 | 156 | 156 | 157 | 157 | 154 |
| | | | | GMT | | | | |
| Day 1 | 8.48 | 7.25 | 8.7 | 8.15 | 9.1 | 75 | 6.96 | 9.1 |
| (95% Cl) | (7-10) | (6-676) | (7.2-11) | (6.74-936) | (753-11) | (6.2-9.08) | (5.76-8.42) | (7.53-11) |
| Day 22 | 107 | 27 | 88 | 163 | 49 | 106 | 160 | 62 |
| (95% Cl) | (78-148) | (19-36) | (64-121) | (118-223) | (36-67) | (77-145) | (117-220) | (45-85) |
| Day 43 | 561 | 111 | 481 | 637 | 170 | 525 | 782 | 225 |
| (95% Cl) | (449-700) | (89-138) | (585-599) | (511-794) | (137-212) | (421-654) | (628-974) | (181-281) |
| | | | | Seroconversion | | | | |
| Day 22, % | 82 | 45 | 78 | 88 | 58 | 82 | 92 | 60 |
| (95% Cl) | (74-87) | (37-53) | (70-84) | (82-93) | (50-86) | (75-87) | (66-96) | (52-68) |
| Day 43,% | 98 | 77 | 97 | 97 | 64 | 99 | 99 | 88 |
| (95% Cl) | (94-100) | (70-83) | (93-99) | (94-99) | (77-89) | (95-100) | (97-100) | (82-93) |

Baseline seropositivity rates (HI titre ≧10) in each group was comparable (18%-27%). All adjuvanted groups satisfied the HI titre ≧1:40 criterion after one dose while unadjuvanted groups met seroprotection criteria only after two doses. Subjects in all vaccine groups (except the unadjuvanted 7.5 μg group) satisfied the seroconversion criterion after dose 1, and all groups met this criterion after two doses.

Sequence variations

As discussed above, reverse genetics was used to prepare reassortants of A/CA/04/2009 with a A/PR/8/34 backbone. During this work three different HA sequences were observed: a wild-type sequence, matching the database sequence for A/CA/04/2009 (referred to as F8); a sequence with a Ser200Pro mutation (F9); and a sequence with a Leu208Ile mutation (F10). NB: residue numbering by H3N2 standards is 14 less than given here.

Transfection of either 293T or MDCK cells with plasmid cocktails containing any of the HA variants produced viable reassortant viruses. No infectious virus was recovered from any simultaneous control transfections with plasmid mixtures lacking a HA gene. Growth of the three reassortants (vF8, vF9, and vF10) was compared to the growth of wild type A/CA/04/2009 and A/PR/8/34 in MDCK cells and in embryonated chicken eggs. Virus titer was assayed by formation of infectious foci on MDCK cells (focus formation assay—FFA) and guinea pig red blood cell agglutination (hemagglutination assay—HA). The wild-type A/CA/04/2009 used for these studies was the same virus used to produce the cloned plasmid DNAs, and it had been passaged only once or twice in MDCK cells.

Figure 11:
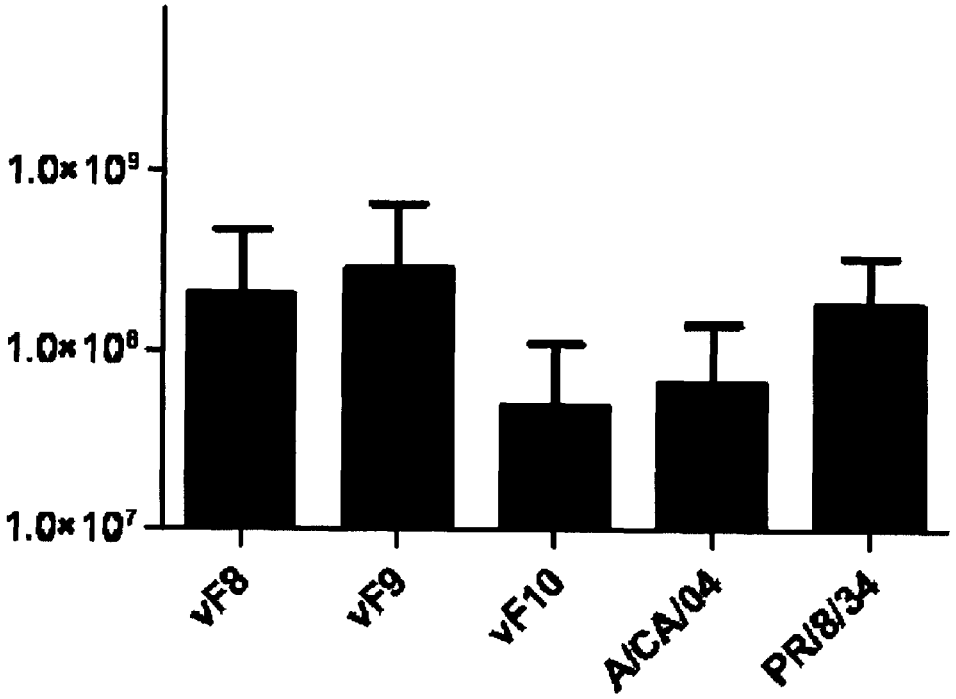
Figure 12:
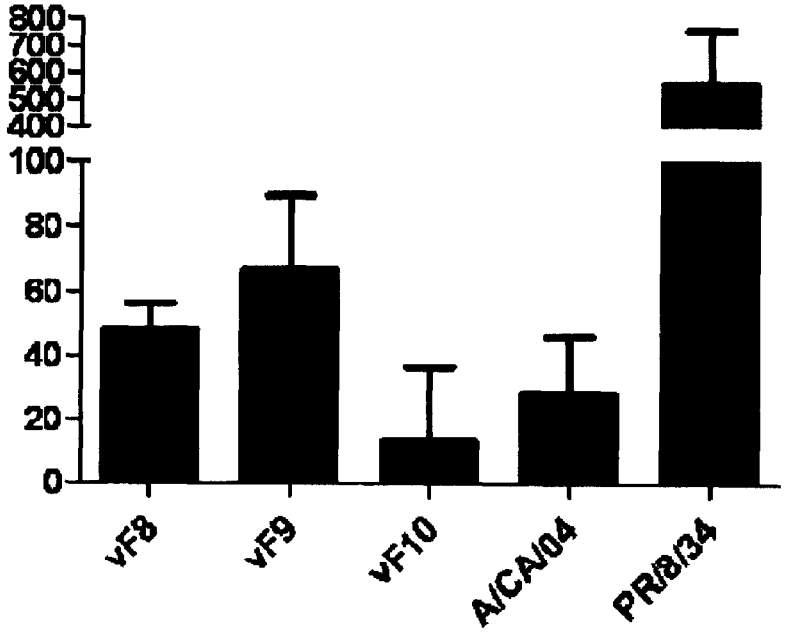

The three reverse genetics reassortants rescued with different HA variants had reproducibly different growth characteristics when grown in MDCK cells and eggs. The F10 variant was significantly less productive by both infectious and HA assays in MDCK cells and in eggs (FIGS. 9-12). The F8 variant grew to approximately 10-fold higher infectious titer and produced more than 4-fold greater HA activity than the other reverse genetics reassortants in MDCK cells (FIGS. 9 & 10), although its performance was comparable to that of the F9 variant in eggs (FIGS. 11 & 12).

To determine if the HA mutations at positions 200 and 208 altered HA antigenicity the hemagglutination inhibition assay (HAI) was assessed with ferret antisera against A/CA/04/2009, A/CA/07/2009, or RG-15 (a reverse genetics-derived A/TX/05/2009-like strain). Databases give identical amino acid sequences from residues 101 to 213 for these three strains. The HAI of all of these antisera with each of the F8-F10 reverse genetics variants were greater than or equivalent to those obtained with A/CA/04/2009, whereas reaction of these variants with normal ferret sera or reaction of A/PR/8/34 virus with these test sera were undetectable. Furthermore, a reverse genetics virus equivalent to F8 with an additional N173D mutation had 8-fold lower HAI titer than A/CA/04. Thus, all of the reverse genetics viruses were antigenically similar to the parental A/CA/04/2009 and A/CA/07/2009 viruses despite the presence of point mutations that improved growth.

Because the variants can increase the growth of reassortants in mammalian cells and eggs, these results demonstrate that sampling viral quasispecies during the rescue of reassortant viruses by reverse genetics can identify useful isolates for vaccine manufacture.

The variable residues at positions 200 and 208 are immediately adjacent to the expected sialic acid binding site. Thus they could affect cell attachment, substrate specificity, growth characteristics, and red blood cell agglutination. These two variations were not reported in two studies that have examined variation in residues near the receptor binding pocket of many H1N1sw isolates [158,159].

It will be understood that the invention has been described by way of example only and modifications may be made whilst remaining within the scope and spirit of the invention.

REFERENCES

[1] WO96/37624.

[2] WO98/46262.

[3] WO95/18861.

[4] Bright et al. (2008) *PLoS ONE* 3:e1501.

[5] Crevar & Ross (2008) *Virology Journal* 5:131.

[6] Vaccines. (eds. Plotkin & Orenstein). 4th edition, 2004, ISBN: 0-7216-9688-0.

[7] WO02/28422.

[8] WO02/067983.

[9] WO02/074336.

[10] WO01/21151.

[11] WO02/097072.

[12] WO2005/113756.

[13] Huckriede et al. (2003) *Methods Enzymol* 373:74-91.

[14] GenBank sequence GI:325176.

[15] McCullers et al. (1999) *J Virol* 73:7343-8.

[16] GenBank sequence GI:325237.

[17] Herlocher et al. (2004) *J Infect Dis* 190(9):1627-30.

[18] Gambaryan & Matrosovich (1992) *J Virol Methods* 39(1-2):111-23.

[19] Mastrosovich et al. (1999) *J Virol* 73: 1146-55.

[20] Stevens et al. (2006) *J Mol Biol* 355:1143-55.

[21] Couceiro & Baum (1994) *Mem Inst Oswaldo Cruz* 89(4):587-91.

[22] Kitikoon et al. (2009) *Vaccine* doi:10.1016/j.vaccine.2009.09.130.

[23] Hoffmann et al. (2002) *Vaccine* 20:3165-3170.

[24] Subbarao et al. (2003) *Virology* 305:192-200.

[25] Liu et al. (2003) *Virology* 314:580-590.

[26] Ozaki et al. (2004) *J. Virol.*78:1851-1857.

[27] Webby et al. (2004) *Lancet* 363:1099-1103.

[28] WO00/60050.

[29] WO01/04333.

[30] US 6649372.

[31] WO2007/002008.

[32] Neumann et al. (2005) *Proc Natl Acad Sci USA* 102:16825-9.

[33] WO2006/067211.

[34] WO01/83794.

[35] Hoffmann et al. (2000) *Virology* 267(2):310-7.

[36] WO97/37000.

[37] Brands et al. (1999) *Dev Biol Stand* 98:93-100.

[38] Halperin et al. (2002) *Vaccine* 20:1240-7.

[39] Tree et al. (2001) *Vaccine* 19:3444-50.

[40] Kistner et al. (1998) *Vaccine* 16:960-8.

[41] Kistner et al. (1999) *Dev Biol Stand* 98:101-110.

[42] Bruhl et al. (2000) *Vaccine* 19:1149-58.

[43] Pau et al. (2001) *Vaccine* 19:2716-21.

[44] WO03/076601.

[45] WO2005/042728.

[46] WO03/043415.

[47] WO01/85938.

[48] WO2006/108846.

[49] EP-A-1260581 (WO01/64846).

[50] WO2006/071563.

[51] WO2005/113758.

[52] WO2006/027698.

[53] WO03/023021

[54] WO03/023025

[55] WO97/37001.

[56] WO01/22992.

[57] Hehme et al. (2004) *Virus Res.* 103(1-2):163-71.

[58] Treanor et al. (1996) *J Infect Dis* 173:1467-70.

[59] Keitel et al. (1996) *Clin Diagn Lab Immunol* 3:507-10.

[60] Zangwill et al. (2008) *J Infect Dis.* 197(4):580-3.

[61] Lundblad (2001) *Biotechnology and Applied Biochemistry* 34:195-197.

[62] *Guidance for Industry: Bioanalytical Method Validation*. U.S. Department of Health and Human Services Food and Drug Administration Center for Drug Evaluation and Research (CDER) Center for Veterinary Medicne (CVM). May 2001.

[63] Ji et al. (2002) *Biotechniques.* 32:1162-7.

[64] Briggs (1991) *J Parenter Sci Technol.* 45:7-12.

[65] Lahijani et al. (1998) *Hum Gene Ther.* 9:1173-80.

[66] Lokteff et al. (2001) *Biologicals.* 29:123-32.

[67] EP-B-0870508.

[68] US 5948410.

[69] WO2007/052163.

[70] *Vaccine Design: The Subunit and Adjuvant Approach* (eds. Powell & Newman) Plenum Press 1995 (ISBN 0-306-44867-X).

[71] US patent 6355271.

[72] Johnson et al. (1999) *Bioorg Med Chem Lett* 9:2273-2278.

[73] Evans et al. (2003) *Expert Rev Vaccines* 2:219-229.

[74] Meraldi et al. (2003) *Vaccine* 21:2485-2491.

[75] Pajak et al. (2003) *Vaccine* 21:836-842.

[76] WO01/22972.

[77] Schellack et al. (2006) *Vaccine* 24:5461-72.

[78] Beignon et al. (2002) *Infect Immun* 70:3012-3019.

[79] Pizza et al. (2001) *Vaccine* 19:2534-2541.

[80] Pizza et al. (2000) *Int J Med Microbiol* 290:455-461.

[81] Scharton-Kersten et al. (2000) *Infect Immun* 68:5306-5313.

[82] Ryan et al. (1999) *Infect Immun* 67:6270-6280.

[83] Partidos et al. (1999) *Immunol Lett* 67:209-216.

[84] Peppoloni et al. (2003) *Expert Rev Vaccines* 2:285-293.

[85] Pine et al. (2002) *J Control Release* 85:263-270.

[86] Tebbey et al. (2000) *Vaccine* 18:2723-34.

[87] Andrianov et al. (1998) *Biomaterials* 19:109-115.

[88] Payne et al. (1998) *Adv Drug Delivery Review* 31:185-196.

[89] US 4,680,338.

[90] US 4,988,815.

[91] WO92/15582.

[92] Stanley (2002) *Clin Exp Dermatol* 27:571-577.

[93] Wu et al. (2004) *Antiviral Res.* 64(2):79-83.

[94] Vasilakos et al. (2000) *Cell Immunol.* 204(1):64-74.

[95] US patents 4689338, 4929624, 5238944, 5266575, 5268376, 5346905, 5352784, 5389640, 5395937, 5482936, 5494916, 5525612, 6083505, 6440992, 6627640, 6656938, 6660735, 6660747, 6664260, 6664264, 6664265, 6667312, 6670372, 6677347, 6677348, 6677349, 6683088, 6703402, 6743920, 6800624, 6809203, 6888000 and 6924293.

[96] Jones (2003) *Curr Opin Investig Drugs* 4:214-218.

[97] WO03/011223.

[98] WO2004/060308.

[99] WO2004/064759.

[100] US 6,924,271.

[101] US2005/0070556.

[102] US 5,658,731.

[103] US patent 5,011,828.

[104] WO2004/87153.

[105] US 6,605,617.

[106] WO02/18383.

[107] WO2004/018455.

[108] WO03/082272.

[109] Wong et al. (2003) *J Clin Pharmacol* 43(7):735-42.

[110] US2005/0215517.

[111] Dyakonova et al. (2004) Int Immunopharmacol 4(13):1615-23.

[112] FR-2859633.

[113] Signorelli & Hadden (2003) *Int Immunopharmacol* 3(8):1177-86.

[114] WO2004/064715.

[115] De Libero et al, *Nature Reviews Immunology,* 2005, 5: 485-496

[116] US patent 5,936,076.

[117] Oki et al, *J. Clin. Investig.,* 113: 1631-1640

[118] US2005/0192248

[119] Yang et al, *Angew. Chem. Int. Ed.,* 2004, 43: 3818-3822

[120] WO2005/102049

[121] Goff et al, *J. Am. Chem., Soc.,* 2004, 126: 13602-13603

[122] WO03/105769

[123] Cooper (1995) *Pharm Biotechnol* 6:559-80.

[124] Gennaro (2000) *Remington: The Science and Practice of Pharmacy.* 20th edition, ISBN: 0683306472.

[125] Banzhoff (2000) *Immunology Letters* 71:91-96.

[126] Nony et al. (2001) *Vaccine* 27:3645-51.

[127] Poole & Mussett (1989) *J Biol Stand* 17:161-71.

[128] Poole et al. (1997) *J. Endotoxin Res* 4:221-31

[129] Potter & Oxford (1979) *Br Med Bull* 35: 69-75.

[130] Greenbaum et al. (2004) *Vaccine* 22:2566-77.

[131] Zurbriggen et al. (2003) *Expert Rev Vaccines* 2:295-304.

[132] Piascik (2003) *J Am Pharm Assoc (Wash DC).* 43:728-30.

[133] Halperin et al. (1979) *Am J Public Health* 69:1247-50.

[134] Herbert et al. (1979) *J Infect Dis* 140:234-8.

[135] Mann et al. (2004) *Vaccine* 22:2425-9.

[136] Chen et al. (2003) *Vaccine* 21:2830-6.

[137] Centers for Diseases Control and Prevention. (2009) MMWR 58:521.

[138] Ershler et al. (2007) *Ann N Y Acad Sci.* 1112:375-84.

[139] Jin et al. (2003) *Virology* 306:1824.

[140] US-6468544.

[141] WO99/64068.

[142] Efferson et al. (2006) *J Virol.* 80(1):383-94.

[143] Munster et al. (2009) *Science* 325:481-3.

[144] Del Giudice et al. (2009) *Sci Transl Med.* 1:12re1.

[145] de Jong et al. (2003) *Dev. Biol (Basel)* 115:63.

[146] Galli et al. (2009) *PNAS USA* 106:7962.

[147] Stephenson et al. (2003) *Vaccine* 21:1687.

[148] Dolin et al. (1977) *J. Infect. Dis.* 136 Suppl., S435.

[149] Caillet et al. (2010) *Vaccine* 28:3076-9.

[150] Quan et al. (2010) *PLoS ONE* 5(2): e9161. doi:10.1371/journal.pone.0009161.

[151] Kistner et al. (2010) *PLoS ONE* 5(2): e9349. doi:10.1371/journal.pone.0009349.

[152] Clark et al. (2009) *NEJM* 361 (10.1056/NEJMoa0907650).

[153] Doroshenko & Halperin (2009) *Expert Rev Vaccines* 8:679-88.

[154] Greenberg et al. (2009) *NEJM* 361 (10.1056/NEJMoa0907413).

[155] Talbot et al. (2008) *Vaccine* 26:4057-61.

[156] Vajo et al. (2010) *Lancet* 375:49-55.

[157] Roman et al. (2010) *Vaccine* 28:1740-45.

[158] Garten et al. (2009) *Science* 325:197-201.

[159] Smith et al. (2009) *Nature* 459:1122-5.

SEQUENCE LISTING

<160> NUMBER OF SEQ ID NOS: 13

<210> SEQ ID NO 1
<211> LENGTH: 566
<212> TYPE: PRT
<213> ORGANISM: Influenza A virus

<400> SEQUENCE: 1

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Ser Ser Trp Ser Tyr Ile
85 90 95

Val Glu Thr Pro Ser Ser Asp Asn Gly Thr Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asn Lys Gly Val Thr Ala Ala Cys Pro His Ala Gly Ala Lys Ser
145 150 155 160

Phe Tyr Lys Asn Leu Ile Trp Leu Val Lys Lys Gly Asn Ser Tyr Pro
165 170 175

Lys Leu Ser Lys Ser Tyr Ile Asn Asp Lys Gly Lys Glu Val Leu Val
180 185 190

Leu Trp Gly Ile His His Pro Ser Thr Ser Ala Asp Gln Gln Ser Leu
195 200 205

Tyr Gln Asn Ala Asp Thr Tyr Val Phe Val Gly Ser Ser Arg Tyr Ser
210 215 220

Lys Lys Phe Lys Pro Glu Ile Ala Ile Arg Pro Lys Val Arg Asp Gln
225 230 235 240

Glu Gly Arg Met Asn Tyr Tyr Trp Thr Leu Val Glu Pro Gly Asp Lys
245 250 255

Ile Thr Phe Glu Ala Thr Gly Asn Leu Val Val Pro Arg Tyr Ala Phe
260 265 270

Ala Met Glu Arg Asn Ala Gly Ser Gly Ile Ile Ile Ser Asp Thr Pro
275 280 285

Val His Asp Cys Asn Thr Thr Cys Gln Thr Pro Lys Gly Ala Ile Asn
290 295 300

Thr Ser Leu Pro Phe Gln Asn Ile His Pro Ile Thr Ile Gly Lys Cys
305 310 315 320

Pro Lys Tyr Val Lys Ser Thr Lys Leu Arg Leu Ala Thr Gly Leu Arg
325 330 335

Asn Ile Pro Ser Ile Gln Ser Arg Gly Leu Phe Gly Ala Ile Ala Gly
340 345 350

Phe Ile Glu Gly Gly Trp Thr Gly Met Val Asp Gly Trp Tyr Gly Tyr

-continued

```
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 2
<211> LENGTH: 326
<212> TYPE: PRT
<213> ORGANISM: Influenza A virus

<400> SEQUENCE: 2

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160
```

-continued

```
Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Thr Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Ile Pro Ser Ile Gln Ser
                325


<210> SEQ ID NO 3
<211> LENGTH: 566
<212> TYPE: PRT
<213> ORGANISM: Influenza A virus

<400> SEQUENCE: 3

Met Lys Ala Lys Leu Leu Val Leu Leu Cys Ala Leu Ser Ala Thr Asp
 1               5                  10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Asn His Asn Gly Lys Leu Cys Lys Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
    130                 135                 140

Val Thr Lys Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205
```

-continued

```
Tyr Arg Lys Glu Asn Ala Tyr Val Ser Val Val Ser Ser His Tyr Asn
    210                 215                 220

Arg Arg Phe Thr Pro Glu Ile Ala Lys Arg Pro Lys Val Arg Asn Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Ile Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 4
<211> LENGTH: 469
<212> TYPE: PRT
<213> ORGANISM: Influenza A virus

<400> SEQUENCE: 4

Met Asn Pro Asn Gln Lys Ile Ile Thr Ile Gly Ser Val Cys Met Thr
```

-continued

```
 1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430
```

```
Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 5
<211> LENGTH: 470
<212> TYPE: PRT
<213> ORGANISM: Influenza A virus

<400> SEQUENCE: 5

Met Asn Pro Asn Gln Lys Ile Ile Thr Ile Gly Ser Ile Cys Met Thr
 1               5                  10                  15

Ile Gly Ile Ile Ser Leu Ile Leu Gln Ile Gly Asn Ile Ile Ser Ile
            20                  25                  30

Trp Val Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
    50                  55                  60

Thr Tyr Val Asn Ile Asn Asn Thr Asn Val Val Ala Gly Lys Asp Thr
65                  70                  75                  80

Thr Ser Val Thr Leu Ala Gly Asn Ser Ser Leu Cys Pro Ile Arg Gly
                85                  90                  95

Trp Ala Ile Tyr Ser Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asp Gly Ala Val Ala Val Leu Lys Tyr
        195                 200                 205

Asn Gly Ile Ile Thr Glu Thr Ile Lys Ser Trp Arg Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Pro Ala Ser Tyr Arg Ile Phe
                245                 250                 255

Lys Ile Glu Lys Gly Lys Ile Thr Lys Ser Ile Glu Leu Asp Ala Pro
            260                 265                 270

Asn Ser His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Lys Gly Ser Cys Asp
```

-continued

```
                325                 330                 335

Pro Val Thr Val Asp Gly Ala Asp Gly Val Lys Gly Phe Ser Tyr Arg
            340                 345                 350

Tyr Gly Asn Gly Val Trp Ile Gly Arg Thr Lys Ser Asn Ser Ser Arg
        355                 360                 365

Lys Gly Phe Glu Met Ile Trp Asp Pro Asn Gly Trp Thr Asp Thr Asp
    370                 375                 380

Ser Asn Phe Leu Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Val Arg Gly Arg Pro Arg
            420                 425                 430

Glu Gly Thr Thr Val Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp Lys
465                 470


<210> SEQ ID NO 6
<211> LENGTH: 566
<212> TYPE: PRT
<213> ORGANISM: Influenza A virus

<400> SEQUENCE: 6

Met Lys Ala Ile Leu Val Val Leu Leu Tyr Thr Phe Ala Thr Ala Asn
 1               5                  10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Pro Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220
```

-continued

```
Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 7
<211> LENGTH: 565
<212> TYPE: PRT
<213> ORGANISM: Influenza A virus

<400> SEQUENCE: 7

Met Lys Ala Ile Leu Val Val Leu Leu Tyr Thr Phe Ala Thr Ala Asn
 1               5                  10                  15

Ala Asp Thr Leu Cys Ile Gly Tyr His Ala Asn Asn Ser Thr Asp Thr
            20                  25                  30
```

-continued

```
Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Gly Val Thr Ala Ala Cys Pro His Ala Gly Ala Lys Ser Phe
145                 150                 155                 160

Tyr Lys Asn Leu Ile Trp Leu Val Lys Lys Gly Asn Ser Tyr Pro Lys
                165                 170                 175

Leu Ser Lys Ser Tyr Ile Asn Asp Lys Gly Lys Glu Val Leu Val Leu
            180                 185                 190

Trp Gly Ile His His Pro Ser Thr Ser Ala Glu Gln Gln Ser Leu Tyr
        195                 200                 205

Gln Asn Ala Asp Thr Tyr Val Phe Val Gly Ser Ser Arg Tyr Ser Lys
    210                 215                 220

Lys Phe Lys Pro Glu Ile Ala Ile Arg Pro Lys Val Arg Asp Gln Glu
225                 230                 235                 240

Gly Arg Met Asn Tyr Tyr Trp Thr Leu Val Glu Pro Gly Asp Lys Ile
                245                 250                 255

Thr Phe Glu Ala Thr Gly Asn Leu Val Val Pro Arg Tyr Ala Phe Ala
            260                 265                 270

Met Glu Arg Asn Ala Gly Ser Gly Ile Ile Ile Ser Asp Thr Pro Val
        275                 280                 285

His Asp Cys Asn Thr Thr Cys Gln Thr Pro Lys Gly Ala Ile Asn Thr
    290                 295                 300

Ser Leu Pro Phe Gln Asn Ile His Pro Ile Thr Ile Gly Lys Cys Pro
305                 310                 315                 320

Lys Tyr Val Lys Ser Thr Lys Leu Arg Leu Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Glu Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445
```

-continued

```
Arg Thr Leu Asp Tyr His Asp Ser Asn Val Lys Asn Leu Tyr Glu Lys
    450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Val Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 8
<211> LENGTH: 325
<212> TYPE: PRT
<213> ORGANISM: Influenza A virus

<400> SEQUENCE: 8

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Gly Val Thr Ala Ala Cys Pro His Ala Gly Ala Lys Ser Phe Tyr
    130                 135                 140

Lys Asn Leu Ile Trp Leu Val Lys Lys Gly Asn Ser Tyr Pro Lys Leu
145                 150                 155                 160

Ser Lys Ser Tyr Ile Asn Asp Lys Gly Lys Glu Val Leu Val Leu Trp
                165                 170                 175

Gly Ile His His Pro Ser Thr Ser Ala Glu Gln Gln Ser Leu Tyr Gln
            180                 185                 190

Asn Ala Asp Thr Tyr Val Phe Val Gly Ser Ser Arg Tyr Ser Lys Lys
        195                 200                 205

Phe Lys Pro Glu Ile Ala Ile Arg Pro Lys Val Arg Asp Gln Glu Gly
    210                 215                 220

Arg Met Asn Tyr Tyr Trp Thr Leu Val Glu Pro Gly Asp Lys Ile Thr
225                 230                 235                 240

Phe Glu Ala Thr Gly Asn Leu Val Val Pro Arg Tyr Ala Phe Ala Met
                245                 250                 255
```

-continued

```
Glu Arg Asn Ala Gly Ser Gly Ile Ile Ile Ser Asp Thr Pro Val His
            260                 265                 270

Asp Cys Asn Thr Thr Cys Gln Thr Pro Lys Gly Ala Ile Asn Thr Ser
        275                 280                 285

Leu Pro Phe Gln Asn Ile His Pro Ile Thr Ile Gly Lys Cys Pro Lys
    290                 295                 300

Tyr Val Lys Ser Thr Lys Leu Arg Leu Ala Thr Gly Leu Arg Asn Ile
305                 310                 315                 320

Pro Ser Ile Gln Ser
                325


<210> SEQ ID NO 9
<211> LENGTH: 565
<212> TYPE: PRT
<213> ORGANISM: Influenza A virus

<400> SEQUENCE: 9

Met Lys Ala Ile Leu Val Val Leu Leu Tyr Thr Phe Ala Thr Ala Asn
 1               5                  10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Gly Val Thr Ala Ala Cys Pro His Ala Gly Ala Ser Ser Phe
145                 150                 155                 160

Tyr Lys Asn Leu Ile Trp Leu Val Glu Lys Gly Asn Ser Tyr Pro Lys
                165                 170                 175

Leu Ser Lys Ser Tyr Ile Asn Asp Lys Gly Lys Glu Val Leu Val Leu
            180                 185                 190

Trp Gly Ile His His Pro Ser Thr Ser Ala Glu Gln Ser Ser Leu Tyr
        195                 200                 205

Gln Asn Ala Asp Thr Tyr Val Phe Val Gly Ser Ser Arg Tyr Ser Lys
    210                 215                 220

Lys Phe Lys Pro Glu Ile Ala Ile Arg Pro Lys Val Arg Asp Gln Ala
225                 230                 235                 240

Gly Arg Met Asn Tyr Tyr Trp Thr Leu Val Glu Pro Gly Asp Lys Ile
                245                 250                 255

Thr Phe Glu Ala Thr Gly Asn Leu Val Val Pro Arg Tyr Ala Phe Ala
            260                 265                 270

Met Glu Arg Asn Ala Gly Ser Gly Ile Ile Ile Ser Asp Thr Pro Val
        275                 280                 285

His Asp Cys Asn Thr Thr Cys Gln Thr Pro Lys Gly Ala Ile Asn Thr
```

-continued

```
    290                 295                 300

Ser Leu Pro Phe Gln Asn Ile His Pro Ile Thr Ile Gly Lys Cys Pro
305                 310                 315                 320

Lys Tyr Val Lys Ser Thr Lys Leu Arg Leu Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Glu Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Tyr His Asp Ser Asn Val Lys Asn Leu Tyr Glu Lys
    450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Val Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 10
<211> LENGTH: 325
<212> TYPE: PRT
<213> ORGANISM: Influenza A virus

<400> SEQUENCE: 10

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95
```

-continued

```
Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Gly Val Thr Ala Ala Cys Pro His Ala Gly Ala Ser Ser Phe Tyr
    130                 135                 140

Lys Asn Leu Ile Trp Leu Val Glu Lys Gly Asn Ser Tyr Pro Lys Leu
145                 150                 155                 160

Ser Lys Ser Tyr Ile Asn Asp Lys Gly Lys Glu Val Leu Val Leu Trp
                165                 170                 175

Gly Ile His His Pro Ser Thr Ser Ala Glu Gln Ser Ser Leu Tyr Gln
            180                 185                 190

Asn Ala Asp Thr Tyr Val Phe Val Gly Ser Ser Arg Tyr Ser Lys Lys
        195                 200                 205

Phe Lys Pro Glu Ile Ala Ile Arg Pro Lys Val Arg Asp Gln Ala Gly
    210                 215                 220

Arg Met Asn Tyr Tyr Trp Thr Leu Val Glu Pro Gly Asp Lys Ile Thr
225                 230                 235                 240

Phe Glu Ala Thr Gly Asn Leu Val Val Pro Arg Tyr Ala Phe Ala Met
                245                 250                 255

Glu Arg Asn Ala Gly Ser Gly Ile Ile Ile Ser Asp Thr Pro Val His
            260                 265                 270

Asp Cys Asn Thr Thr Cys Gln Thr Pro Lys Gly Ala Ile Asn Thr Ser
        275                 280                 285

Leu Pro Phe Gln Asn Ile His Pro Ile Thr Ile Gly Lys Cys Pro Lys
    290                 295                 300

Tyr Val Lys Ser Thr Lys Leu Arg Leu Ala Thr Gly Leu Arg Asn Ile
305                 310                 315                 320

Pro Ser Ile Gln Ser
                325


<210> SEQ ID NO 11
<211> LENGTH: 566
<212> TYPE: PRT
<213> ORGANISM: Influenza A virus

<400> SEQUENCE: 11

Met Lys Ala Ile Leu Val Val Leu Leu Tyr Thr Phe Ala Thr Ala Asn
 1               5                  10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140
```

-continued

```
Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Thr Phe Lys Pro Glu Ile Ala Ile Arg Pro Lys Val Arg Asp Arg
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560
```

-continued

```
Gln Cys Arg Ile Cys Ile
                565


<210> SEQ ID NO 12
<211> LENGTH: 326
<212> TYPE: PRT
<213> ORGANISM: Influenza A virus

<400> SEQUENCE: 12

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Lys
        195                 200                 205

Thr Phe Lys Pro Glu Ile Ala Ile Arg Pro Lys Val Arg Asp Arg Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Ile Pro Ser Ile Gln Ser
                325


<210> SEQ ID NO 13
<211> LENGTH: 566
<212> TYPE: PRT
<213> ORGANISM: Influenza A virus
```

<400> SEQUENCE: 13

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Ser Ser Trp Ser Tyr Ile
85 90 95

Val Glu Thr Pro Ser Ser Asp Asn Gly Thr Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asn Lys Gly Val Thr Ala Ala Cys Pro His Ala Gly Ala Lys Ser
145 150 155 160

Phe Tyr Lys Asn Leu Ile Trp Leu Val Lys Lys Gly Asn Ser Tyr Pro
165 170 175

Lys Leu Ser Lys Ser Tyr Ile Asn Asp Lys Gly Lys Glu Val Leu Val
180 185 190

Leu Trp Gly Ile His His Pro Ser Thr Ser Ala Asp Gln Gln Ser Ile
195 200 205

Tyr Gln Asn Ala Asp Thr Tyr Val Phe Val Gly Ser Ser Arg Tyr Ser
210 215 220

Lys Lys Phe Lys Pro Glu Ile Ala Ile Arg Pro Lys Val Arg Asp Gln
225 230 235 240

Glu Gly Arg Met Asn Tyr Tyr Trp Thr Leu Val Glu Pro Gly Asp Lys
245 250 255

Ile Thr Phe Glu Ala Thr Gly Asn Leu Val Val Pro Arg Tyr Ala Phe
260 265 270

Ala Met Glu Arg Asn Ala Gly Ser Gly Ile Ile Ile Ser Asp Thr Pro
275 280 285

Val His Asp Cys Asn Thr Thr Cys Gln Thr Pro Lys Gly Ala Ile Asn
290 295 300

Thr Ser Leu Pro Phe Gln Asn Ile His Pro Ile Thr Ile Gly Lys Cys
305 310 315 320

Pro Lys Tyr Val Lys Ser Thr Lys Leu Arg Leu Ala Thr Gly Leu Arg
325 330 335

Asn Ile Pro Ser Ile Gln Ser Arg Gly Leu Phe Gly Ala Ile Ala Gly
340 345 350

Phe Ile Glu Gly Gly Trp Thr Gly Met Val Asp Gly Trp Tyr Gly Tyr
355 360 365

His His Gln Asn Glu Gln Gly Ser Gly Tyr Ala Ala Asp Leu Lys Ser
370 375 380

Thr Gln Asn Ala Ile Asp Glu Ile Thr Asn Lys Val Asn Ser Val Ile
385 390 395 400

Glu Lys Met Asn Thr Gln Phe Thr Ala Val Gly Lys Glu Phe Asn His

-continued

```
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

The invention claimed is:

1. A method for immunizing a subject, comprising administering two separate doses of unadjuvanted monovalent influenza vaccine to the subject, wherein (a) the two doses are administered from 1-6 weeks apart, and (b) each monovalent vaccine contains a H1 subtype influenza A virus hemagglutinin which is more closely related to SEQ ID NO: 1 than to SEQ ID NO: 3.

2. A method for immunizing a subject, comprising administering two separate doses of unadjuvanted monovalent influenza vaccine to the subject, wherein (a) the two doses are administered from 1-6 weeks apart, and (b) each monovalent vaccine contains a H1 subtype influenza A virus hemagglutinin which has at least 85% sequence identity to SEQ ID NO: 1.

3. A method for immunizing a subject, comprising administering to them by an intradermal route an unadjuvanted immunogenic composition comprising a H1 subtype influenza A virus hemagglutinin which is more closely related to SEQ ID NO: 1 than to SEQ ID NO: 3.

4. A method for immunizing a subject, comprising administering to them by an intradermal route an unadjuvanted immunogenic composition comprising a H1 subtype influenza A virus hemagglutinin which has at least 85% sequence identity to SEQ ID NO: 1.

* * * * *